(12) United States Patent
Shafrir et al.

(10) Patent No.: US 12,138,176 B2
(45) Date of Patent: Nov. 12, 2024

(54) IMPLANT AND COVERING METHODS AND APPARATUS

(71) Applicant: SPINOL Ltd., Modi'in (IL)

(72) Inventors: Roey Shafrir, Modi'in (IL); Shahar Dror, Tel Aviv (IL); Michael M. Sahar, Be'erotayim (IL); Haim Shlalom Shnider, Netanya (IL); Arnon Moshaiuf, Atlit (IL)

(73) Assignee: Spinol Ltd., Modi'in (IL)

( * ) Notice: Subject to any disclaimer, the term of this patent is extended or adjusted under 35 U.S.C. 154(b) by 0 days.

(21) Appl. No.: 18/170,627

(22) Filed: Feb. 17, 2023

(65) Prior Publication Data

US 2023/0190488 A1   Jun. 22, 2023

Related U.S. Application Data

(63) Continuation of application No. 16/691,310, filed on Nov. 21, 2019, now abandoned.

(60) Provisional application No. 62/770,512, filed on Nov. 21, 2018.

(51) Int. Cl.
  *A61F 2/44*    (2006.01)
  *A61F 2/28*    (2006.01)
  *A61F 2/30*    (2006.01)

(52) U.S. Cl.
  CPC ........ *A61F 2/442* (2013.01); *A61F 2002/285* (2013.01); *A61F 2002/30205* (2013.01); *A61F 2002/3021* (2013.01)

(58) Field of Classification Search
  CPC .............. A61F 2/442; A61F 2002/4435; A61F 2002/4495
  See application file for complete search history.

(56) References Cited

U.S. PATENT DOCUMENTS

| | | | |
|---|---|---|---|
| 6,860,895 B1 | 3/2005 | Akerfeldt et al. | |
| 8,382,840 B2 * | 2/2013 | Hestad | A61F 2/4611 606/86 A |
| 8,906,059 B2 | 12/2014 | McGuckin et al. | |

(Continued)

FOREIGN PATENT DOCUMENTS

| | | |
|---|---|---|
| CN | 108024859 A | 5/2018 |
| DE | 10 2015 112799 A1 | 2/2017 |

(Continued)

OTHER PUBLICATIONS

International Search Report and Written Opinion for International Application No. PCT/IB2019/001245 mailed May 27, 2020.

(Continued)

*Primary Examiner* — Matthew J Lawson
(74) *Attorney, Agent, or Firm* — Wolf, Greenfield & Sacks, P.C.

(57) ABSTRACT

In some aspects, a device comprising an implant configured for insertion into a portion of human anatomy, and at least one covering coupled to the implant is provided. According to some aspects, the implant comprises one or more protrusions configured to prevent leakage of material and/or to resist displacement of the implant. According to some aspects, the covering is configured to facilitate improved leakage and/or implant displacement prevention.

22 Claims, 28 Drawing Sheets

(56) References Cited

U.S. PATENT DOCUMENTS

| | | | |
|---|---|---|---|
| 2002/0128713 A1* | 9/2002 | Ferree | A61F 2/4465 623/17.11 |
| 2002/0165561 A1* | 11/2002 | Ainsworth | A61B 17/1227 606/151 |
| 2003/0074075 A1 | 4/2003 | Thomas et al. | |
| 2003/0078579 A1* | 4/2003 | Ferree | A61F 2/442 606/53 |
| 2004/0024463 A1* | 2/2004 | Thomas, Jr. | A61F 2/4611 623/17.16 |
| 2007/0162131 A1* | 7/2007 | Friedman | A61F 2/442 623/17.11 |
| 2008/0065218 A1 | 3/2008 | O'Neil | |
| 2009/0036937 A1 | 2/2009 | Cauthen, III et al. | |
| 2011/0071580 A1 | 3/2011 | Seifert et al. | |
| 2012/0245623 A1 | 9/2012 | Kariniemi et al. | |
| 2013/0338778 A1* | 12/2013 | Drori | A61B 17/0057 623/17.16 |
| 2015/0094815 A1 | 4/2015 | Drori et al. | |
| 2018/0161142 A1 | 6/2018 | Finger et al. | |
| 2019/0274844 A1 | 9/2019 | Seifert et al. | |
| 2020/0188127 A1 | 6/2020 | Shafrir et al. | |

FOREIGN PATENT DOCUMENTS

| | | |
|---|---|---|
| RU | 2140229 C1 | 10/1999 |
| RU | 2244527 C2 | 1/2005 |
| WO | WO 2007/083288 A2 | 7/2007 |
| WO | WO 2012/120509 A1 | 9/2012 |

OTHER PUBLICATIONS

International Preliminary Report on Patentability for International Application No. PCT/IB2019/001245 mailed Jun. 3, 2021.

Extended European Search Report mailed Jun. 24, 2022 in connection with European Application No. EP19886432.4.

* cited by examiner

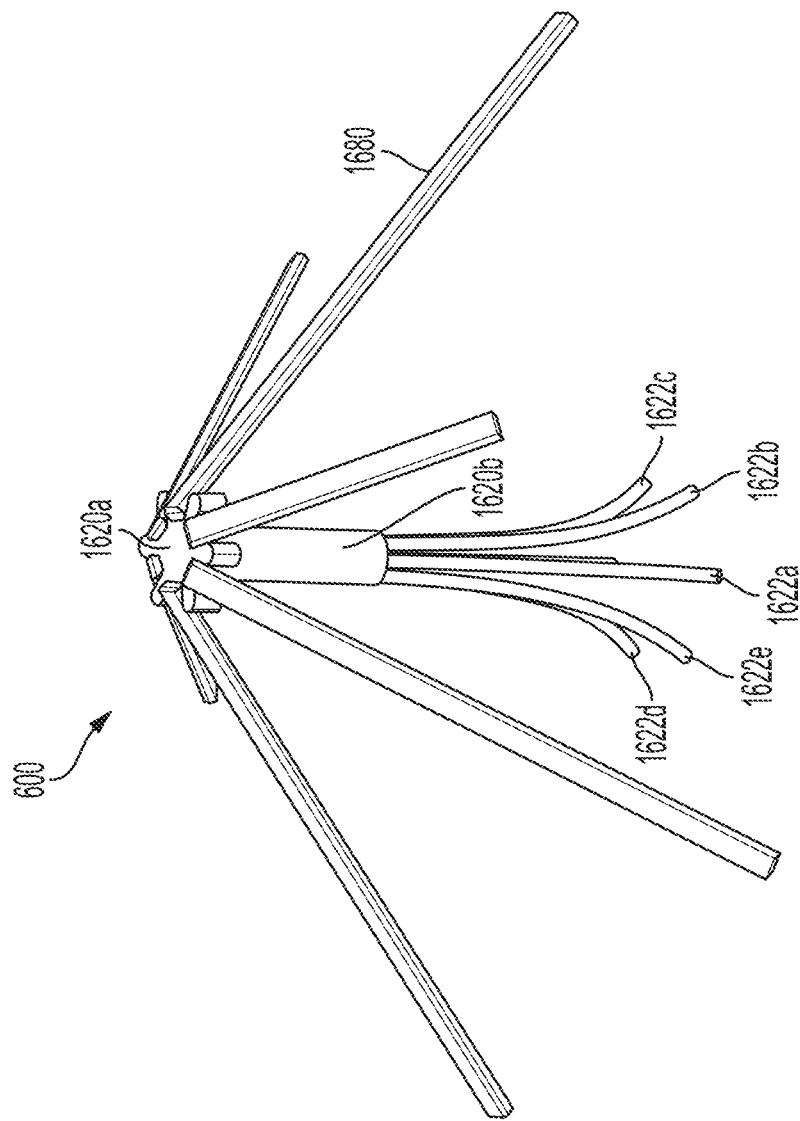
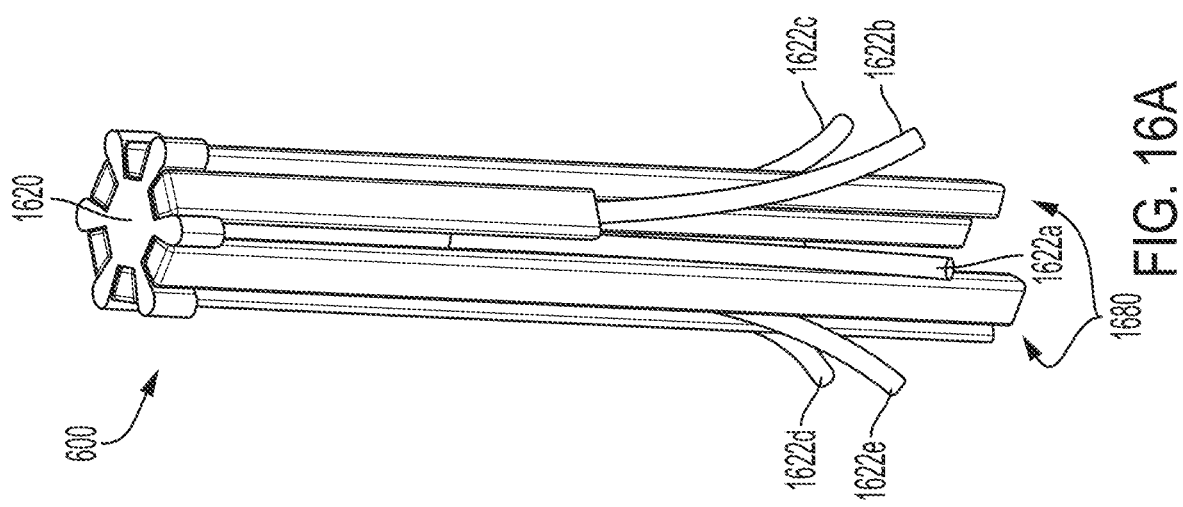
FIG. 16B
FIG. 16A

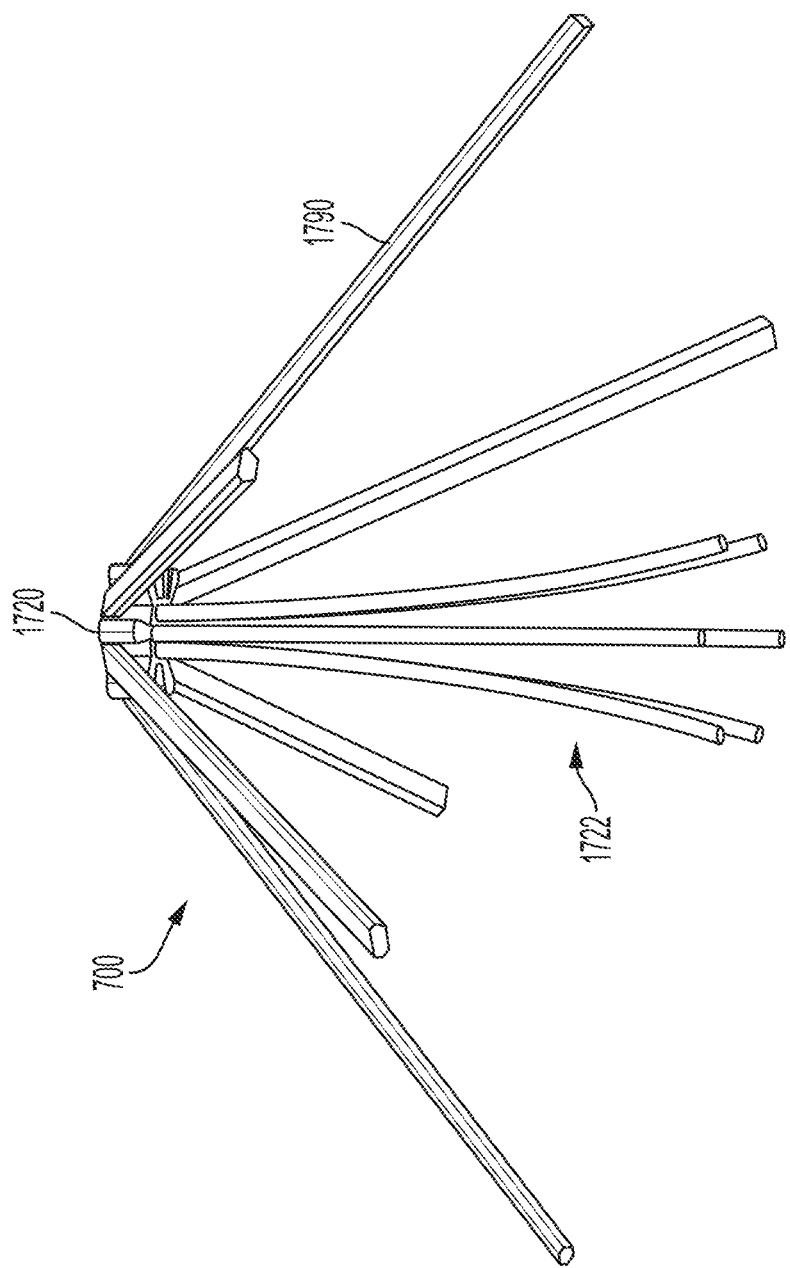

IMPLANT AND COVERING METHODS AND APPARATUS

RELATED APPLICATIONS

This application claims the benefit under 35 U.S.C. § 120 and is a continuation of U.S. application Ser. No. 16/691,310, filed Nov. 21, 2019, entitled "Implant and Covering Methods and Apparatus", which claims priority under 35 U.S.C. § 119 to U.S. Provisional Application No. 62/770,512, filed Nov. 21, 2018 and titled "Implant Membrane Methods and Apparatus," each application of which is herein incorporated by reference in its entirety.

BACKGROUND

Techniques described herein relate generally to the field of implantable devices for the closure of biological defects, and more particularly to an implant arranged to securely seal an intervertebral disc defect.

The human spine, known technically as the vertebral column, is constituted of a plurality of articulating vertebrae, and extending downwards towards fused vertebrae in the sacrum and coccyx. Using standard anatomical terminology, the vertebral column is found in the dorsal aspect of the torso. The articulating vertebrae are separated from adjacent vertebrae on either side by an intervertebral disc (or vertebral disc for short) which forms a cartilaginous joint to allow slight movement of the vertebrae, and further acts to hold the various vertebrae together so as to form the vertebral column. The vertebral disc also provides shock absorption for stresses resulting from movement of the body.

Each intervertebral disc comprises an outer annulus fibrosus, often simply called the annulus, which surrounds and contains biological material, called nucleus pulposus, which is a jelly-like substance that functions to distribute hydraulic pressure within each intervertebral disc under compressive loads. In the event of an intervertebral disc defect, such as a prolapsed or herniated disc, the nucleus pulposus is often forced out through the defect of the annulus, and may apply pressure to nearby nerves or to the spinal cord. In severe cases, the escaping nucleus pulposus may cause chemical irritation of nearby nerve roots. Protrusion of the nucleus pulposus may be variously referred to as a disc bulge, a herniated disc, a ruptured disc or a sequestered disc, depending on the specific diagnosis.

In order to avoid confusion in describing medical devices, certain fixed terminology is utilized. In particular, the term proximal usually means closer to the surgeon, unless otherwise stated, and the word distal usually means further from the surgeon, unless otherwise stated. Surgery to repair a defect in the annulus is usually performed from the patient's dorsal side, i.e. from the back, and thus the terms proximal and distal are understood with the surgeon approaching from the patient's back. However this orientation is not meant to be limiting in any way. In the event of surgery performed ventrally, the terms need to be understood in relation to a dorsal operation. Again using the surgeon as the point of reference, the distal direction is generally in the direction of insertion of an implant (generally away from the surgeon) and the proximal direction is generally in the opposing direction.

While various schemes for repair of annulus defects are known, one common solution is a surgical procedure known as discectomy, which involves the surgical removal of the herniated disc material. Discectomy is often performed in conjunction with a laminectomy, where a small piece of bone, known as the lamina, is removed from the affected vertebra, allowing the surgeon to better see and access the area of disc herniation.

SUMMARY

According to some embodiments, a device comprising an implant and at least one covering coupled to the implant is provided. The device may be configured for insertion into a portion of human anatomy, such as a defect of a vertebral disc. According to some aspects, the implant comprises one or more protrusions configured to prevent leakage of material from the defect and/or to resist displacement of the implant. According to some aspects, the covering is configured to facilitate improve the performance in preventing leakage and/or preventing implant displacement.

According to some embodiments, the at least one covering comprises a covering coupled towards a distal end of the implant and, according to some embodiments, the at least one covering comprises a covering coupled towards a proximal end of the implant. Some embodiments include at least one covering that is open at a distal end and some embodiments include at least one covering is closed at a distal end. Some embodiments include a first covering coupled towards a distal end of the implant and a second covering coupled proximally from the first covering. According to some embodiments, at least one covering has a frustoconical shape.

According to some embodiments, the implant comprises at least one protrusion. In some embodiments, at least one covering is coupled to the at least one protrusion. According to some embodiments at least one covering is fitted to the at least one protrusion. Some embodiments include a covering that is open to form a sleeve for the at least one protrusion and some embodiments include a covering that is closed to form a sheath for the at least one protrusion. According to some embodiments, the implant comprises a plurality of protrusions, and at least one covering is fitted to the plurality of protrusions, either separately fitted to individual protrusions or fitted to multiple protrusions.

According to some embodiments, the device comprises a support structure coupled to the implant, wherein the at least one covering is directly coupled to the support structure. According to some embodiments, the support structure is formed in the shape of a coil and at least one covering is coupled to the coil. According to some embodiments, the support structure comprises a plurality of ribs and at least one covering is coupled to the plurality of ribs.

According to some embodiments, the implant is constructed using a first material and the at least one covering comprises a bio-compatible material different than the first material, for example, a polymer, synthetic material, a biological substance and/or material based on human tissue. In some embodiments, at least one covering comprises flexible and/or conformable material.

According to some embodiments, the at least one covering is coupled to the implant prior to insertion of the implant into the portion of the human anatomy, and in some embodiments, the at least one covering is coupled to the implant after insertion of the implant into the portion of the human anatomy. According to some embodiments, the device is configured to be inserted into an intervertebral disc through a defect in the disc and the implant comprises at least one protrusion configured to facilitate prevention of leakage from the defect and/or to resist displacement of the implant through the defect. According to some embodiments, the at least one covering is configured to improve leakage prevention and/or improve resistance to displacement of the implant.

According to some embodiments, the implant and/or the at least one covering are configurable between an insertion configuration suitable for insertion into biological anatomy and a deployed configuration configured to facilitate prevention of leakage and/or to resist displacement of the implant. According to some embodiments, the biological anatomy comprises an intervertebral disc having a defect, and wherein the implant and/or the at least one covering is configurable between an insertion configuration suitable for insertion into the intervertebral disc via the defect and a deployed configuration configured to facilitate prevention of leakage from the intervertebral disc and/or to resist displacement of the implant from the intervertebral disc.

BRIEF DESCRIPTION OF DRAWINGS

FIG. 16A illustrates an implant in a closed or insertion configuration, in accordance with some embodiments;

FIG. 16B illustrates the implant illustrated in FIG. 16A in an open or deployed configuration, in accordance with some embodiments;

FIG. 17 illustrates an implant in an open or deployed configuration, in accordance with some embodiments;

DETAILED DESCRIPTION

Figure 1A:
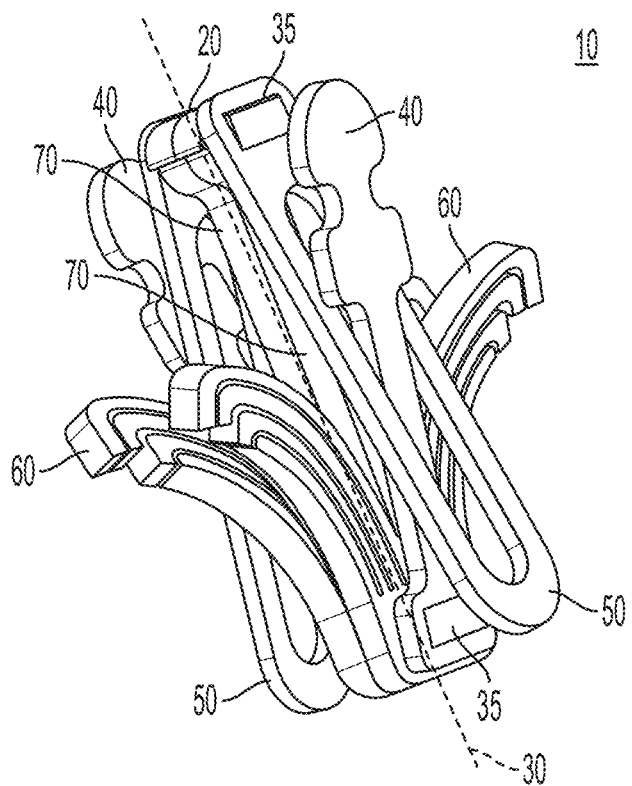
FIGS. 1A, 1B, and 1D illustrate an implant in an open or deployed configuration, in accordance with some embodiments.

As discussed above, performing a discectomy is a common surgical procedure to treat a herniated disc. One problem with discectomy procedures (with or without an accompanying laminectomy) is that additional nucleus pulposus material may leak from the annulus over time by the unsealed defect in the annulus, which is not sealed by the discectomy operation. The terms "leak" or "leakage" refer herein to generally unwanted movement of material external to target anatomy, including biological material or other material inserted or implanted during surgery. Leakage includes protrusion of nucleus pulposus material from an intervertebral disc, as well as any other exposure of internal material external to target anatomy.

Conventional techniques for sealing a defect have included inserting implant material into the defect and positioning the material over the defect. However, such conventional techniques were susceptible to shifting, migration or other displacement of the material from its correctly deployed position, thus opening the defect and allowing leakage of material. In some instances, these conventional techniques resulted in the material being shifted back into the defect or even ejected so that a portion of the material would protrude from the defect causing complications in addition degrading or eliminating leakage protection. To address these deficiencies, the Applicant developed an implant device and associated procedures to improve performance of sealing or closure of an annulus defect, some examples of which are described in U.S. patent application Ser. No. 13/146,403 to Shafrir et al., entitled "Implantable Device for Sealing a Spinal Annular Fissure Tear and Method for Deploying the Same," published on Nov. 17, 2011 as U.S. Publication No. 2011/0282456, the subject matter of which is herein incorporated by reference in its entirety.

Further examples of exemplary implant devices are described in U.S. Pat. No. 9,526,623, issued on Dec. 27, 2016 and entitled "Spinal Disc Annulus Closure Device," the subject matter of which is herein incorporated by reference in its entirety. One of the challenges of such implant devices is the need to stand up to strong hydrostatic displacement forces while not interfering with a full range of motion of the vertebral column over an expected patient lifetime. Techniques addressing this challenge are described in International Application No. PCT/IL2019/050263 (hereinafter "the '263 PCT Application), the subject matter of which is herein incorporated by reference in its entirety.

The inventors have developed techniques to improve the performance of the exemplary implant devices described in the above incorporated references and discussed in further detail below. In particular, techniques described herein may improve the ability of the implant device to seal the annulus against further release of material, such as nucleus pulposus material or other injected material, through the defect during the recuperation from the surgery thereafter, prevent material of various viscosities from leaking from the defect and/or resist displacement of the implant, while allowing for a full range of motion of the vertebral column, ideally over an expected patient lifetime without experiencing fatigue failure.

According to some embodiment, one or more of the above described improvements may be facilitated by providing a covering coupled to the implant. A "covering" refers herein to a component that can be coupled to, either directly or indirectly, or otherwise deployed proximate an implant to facilitate leakage prevention and/or to improve the resulting devices resistance to displacement of the implant. A covering is typically fabricated from a material different than material from which the implant is constructed, though in some embodiments the same material may be used (e.g., a covering may be made from a mesh or woven fibers of the same material as the implant). A covering may include one or more sheets, skins and/or membranes (terms that are used interchangeably herein unless otherwise specified) that are coupled to the implant device to provide improved leakage and/or implant displacement protection or prevention.

The covering may be configured in the general form of a hat, hood, umbrella, skirt, sheath, sleeve, or other suitable configuration that resists leakage and/or implant displacement, examples of which are described in detail below. According to some embodiments, a covering is coupled to the implant prior to inserting the implant into the biological anatomy (e.g., into an annulus of a vertebral disc) and, according to other embodiments, the covering is coupled to the implant device post-insertion. According to some embodiments, a covering is configured so that it can be transitioned between a closed or insertion configuration suitable for insertion into biological anatomy and an open or deployed configuration after insertion has been completed.

By coupling a covering to an implant that is itself configured to prevent leakage and to resist displacement of the implant, the resulting device significantly improves the performance of the device. The term "displacement" refers generally to shifting or movement of an implant and/or covering from its desired deployed position. As discussed above, conventional devices were vulnerable to forces that cause the device to be displaced from its position over a defect in anatomy, degrading the ability of the device to prevent leakage and/or causing further complications should the displaced implant protrude from the defect or otherwise shift so that the device no longer performs adequately. Accordingly, devices comprising an implant and a covering coupled thereto developed by the inventors and described herein exhibit significantly improved performance in preventing leakage and resisting displacement.

Following below are more detailed descriptions of various concepts related to, and embodiments of, a covering for an implant device configured for insertion into biological anatomy, for example, a herniated vertebral disc. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein. For example, while aspects of exemplary coverings are illustrated and described in connection with the implant device generally described in the '263 PCT Application, it should be appreciated that one or more coverings described herein may be coupled to virtually any type of implant, including the different implants described in the above incorporated references.

Figure 1B:
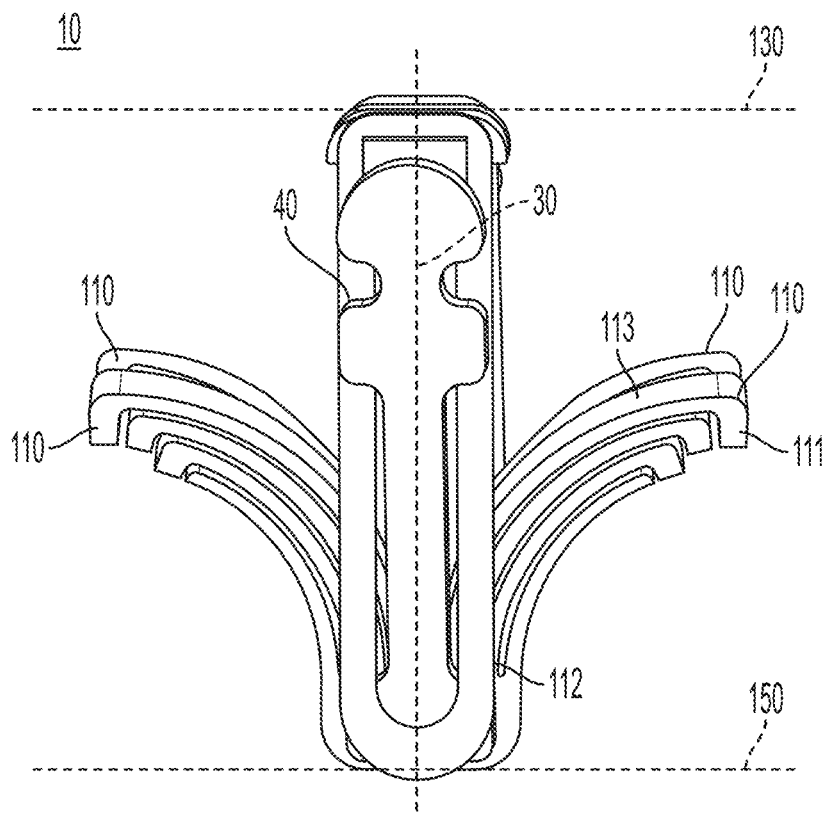

FIGS. 1A and 1B illustrate an exemplary implant 10 to which a covering may be coupled, in accordance with some embodiments. In FIGS. 1A and 1B, implant 10 is illustrated in an open or deployed configuration configured to facilitate prevention of leakage and/or to resist displacement of the implant. Implant 10 comprises a body 20 exhibiting a longitudinal axis 30. Implant 10 comprises a plurality of protrusions that extend outward from the longitudinal axis 30 of body 20. For example, the plurality of protrusions of exemplary implant 10 comprise a pair of proximal arms 40, a pair of distal arms 50, and a pair of intermediate arm assemblies 60. Proximal arms 40 and distal arms 50 may include connection members 35 that couple the arms to body 20. Each protrusion 60 may further comprise a pair of intermediate arms 110 having a first 111, a second end 112, and a face 113 providing flexibility and stability for protrusions 60. Body 20 comprises a pair of sections 70. Implant 10 may be formed from a bio-compatible material. In one non-limiting embodiment, implant 10 may be formed partially, substantially or entirely of a shape memory alloy, for example, Nitinol.

Figure 2:
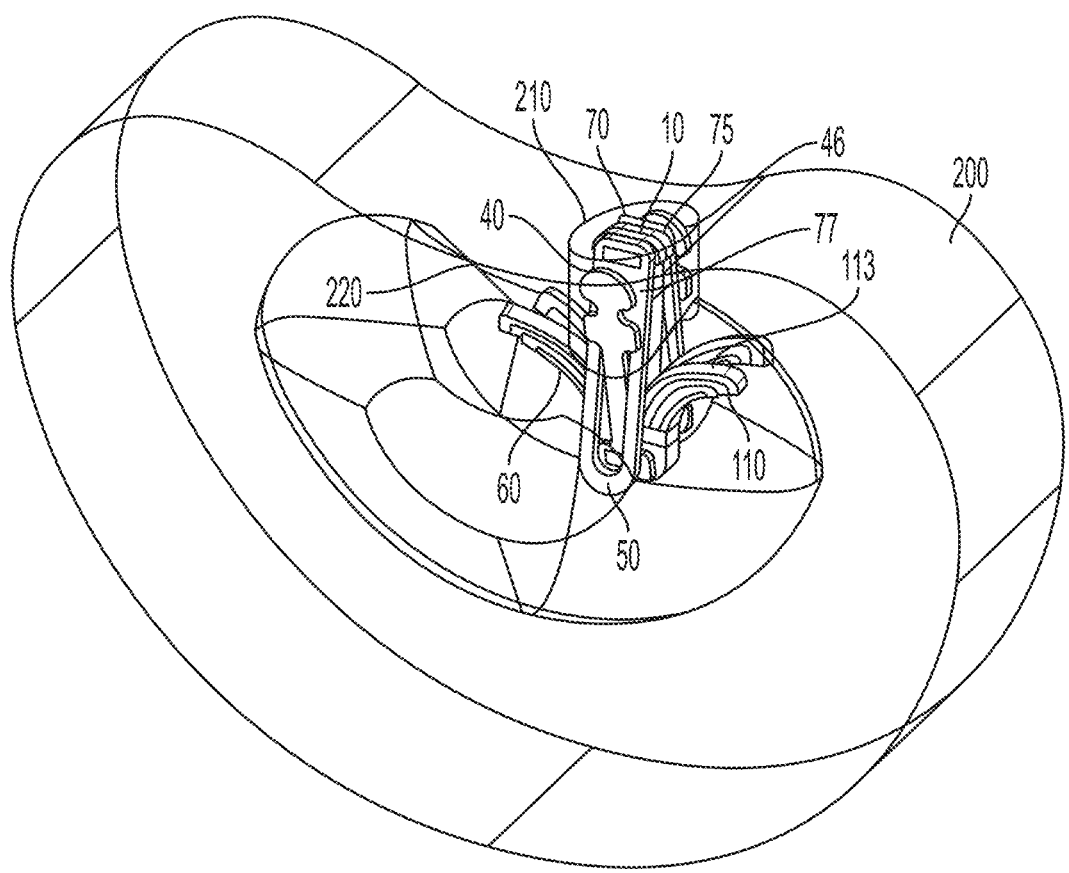
FIG. 2 illustrates an implant deployed to seal a defect in a vertebral disc, in accordance with some embodiments.

The protrusions extending from longitudinal axis 30 of body 20 (e.g., protrusions 60, 50, 40, etc.) facilitate leakage protection and facilitate preventing the implant from being displaced after implantation, as shown by the expanded implant shown in the open or deployed configuration within the annulus in FIG. 2. The protrusions may also facilitate production and adhesion of scar tissue to the implant to further facilitate leakage prevention and resistance to displacement.

Figure 1C:
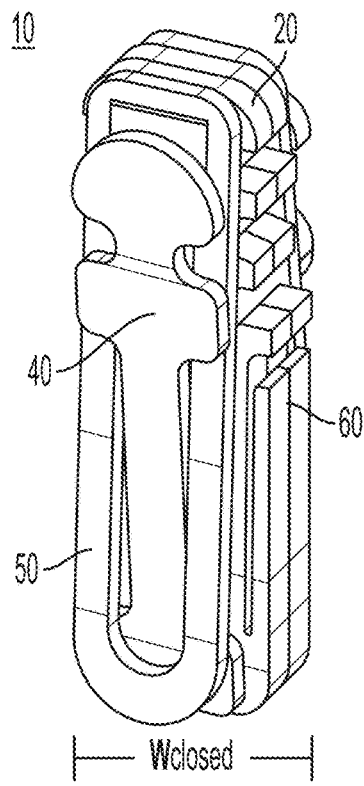
FIG. 1C illustrates the implant illustrated in FIGS. 1A, 1B and 1D in a closed or insertion configuration.

Implant 10 may be configured to be inserted into a defect in the annulus of a vertebral disc by first placing implant 10 in an insertion or closed configuration, as illustrated in FIG. 1C. In particular, implant 10 may be transitioned between the closed or insertion configuration (shown in FIG. 1C) adapted for insertion, for example, into a vertebral disc (e.g., via a defect to be sealed by the implant) and an open or deployed configuration (shown in FIGS. 1A, 1B and 2) adapted to facilitate prevention of leakage from the defect and/or to resist displacement of the implant through the defect. In the closed/insertion configuration, protrusions 40, 50 and 60 are configured close to body 20 to make the implant narrow enough to fit through an insertion corridor into biological anatomy (e.g., narrow enough to pass through a defect in the annulus of a vertebral disc). Once the implant has been inserted into the annulus, the implant expands into its deployed configuration as illustrated in FIG. 2. Specifically, the plurality of protrusion expand away from the body 20 such that it can withstand the forces acting on it created by the movements and loading on a spine under ordinary daily movement, activity and behaviour.

Figure 1D:
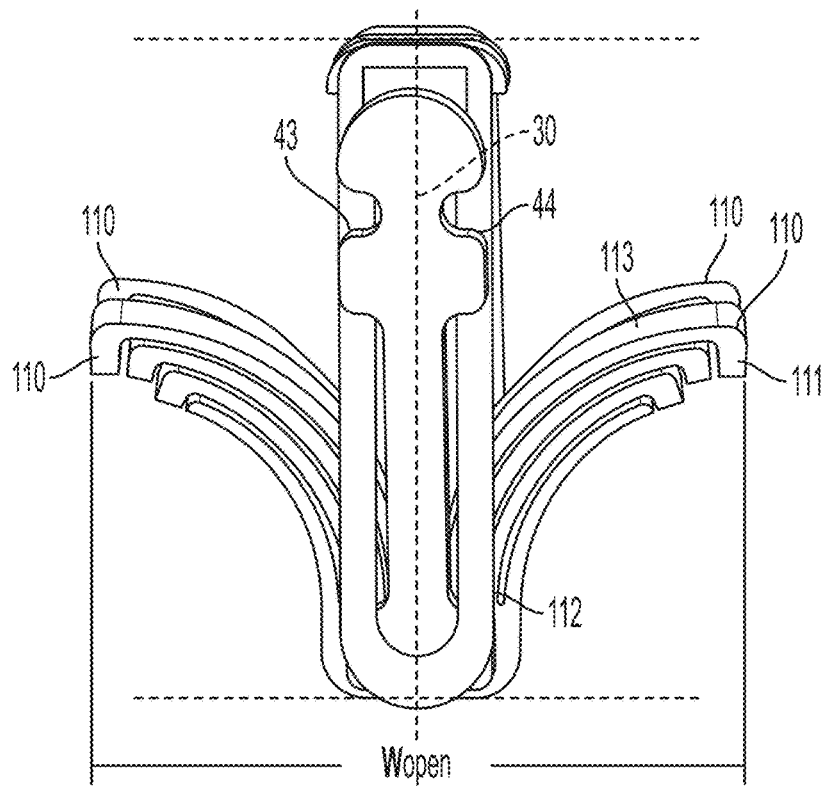

As shown in FIGS. 1C and 1D, the maximum dimension of the implant in a direction generally perpendicular to the longitudinal axis of the device (e.g., perpendicular to the axis of insertion), labelled as $W_{closed}$, is small in the closed configuration relative to this same maximum dimension of the implant, labelled as $W_{open}$, in the open configuration. In this manner, an implant can be transitioned from a configuration suitable for insertion through relatively small defects and then expanded significantly after deployment (e.g., as shown in FIG. 2) to provide excellent performance in preventing leakage and resisting implant displacement. According to some embodiment, the ratio of $W_{open}$ to $W_{closed}$ is at least 2 (e.g., $W_{open}$ is at least twice that of $W_{closed}$), for example, between 2 and 5. According to some embodiments, the ratio of $W_{open}$ to $W_{closed}$ is at least 3, for example, between 3 and 10. It should be appreciated that the ratio may be designed to exhibit a desired ratio (e.g., a ratio of 2, 2.5, 3, 3.5, 4, 4.5, 5, 6, 8, or more, or any other suitable ratio).

Additional details regarding properties of implant 10 are described in the '263 PCT Application, along with an exemplary delivery system, including a tool and a grip for the implant configured to assist a surgeon in inserting and deploying the implant. For example, such an exemplary delivery system is illustrated in FIG. 3A-3D of the incorporated '263 PCT Application and described in the accompanying description therein. The exemplary delivery system described in the '263 PCT application is one example of a suitable system for assisting a surgeon in implanting the devices described herein, both respect to the implant and embodiments of coverings described herein. It should be appreciated that other methods of inserting an implantable device may be used, as the aspects are not limited in this respect.

FIG. 2 illustrates implant 10 in a deployed configuration after surgical insertion into an annulus 200 to facilitate closure of the biological defect 210 of the annulus. Implant 10 is positioned such that first ends 75 of sections 70 and second ends 46 of proximal 20 arms 40 are within defect 210. Intermediate arm assemblies 60 are juxtaposed with defect 210 such that first face 113 of the intermediate arms 110 closest to middle portions 77 face an inner wall 220 in the vicinity of the defect. Intermediate arms 110, proximal arms 40 and distal arms 50 together provide a variety of anchoring points for implant 10 to withstand and oppose forces applied to implant 10 from annulus 200, thereby preventing displacement or migration of implant 10 within or out of annulus 200.

As discussed above, the inventors have developed techniques to facilitate preventing leakage of material (e.g., nucleus pulposus) from biological anatomy, for example, preventing leakage from a defect, and/or to increase resistance to displacement of the implant. According to some embodiments, at least one covering coupled to a portion of the implant is provided. A covering may be coupled to the implant either directly or indirectly and may be removable or permanently attached to the implant. According to some embodiments, a covering is coupled to one or more protrusions of an implant to improve the leakage and/or implant displacement prevention. According to some embodiments, a covering is coupled indirectly to an implant via a support structure that is directly coupled to the implant. According to some embodiments, a covering resists movement of material to facilitate leakage prevention (including materials with a lower viscosity than nucleus pulposus) and/or to resist motion of implant to protect against displacement of the implant.

According to some embodiments, a covering comprises at least one sheet made of bio compatible material, such as a fabric that may be porous woven, unwoven, or non-porous. The at least one sheet forming a covering may be made from polymer, synthetic and/or biological material and/or may be based on human tissue. The at least one sheet may be flexible so as to conform to the contours of the implant, the portion of the implant to which the covering is coupled, or to a support structure to which the at least one sheet is coupled. The at least one sheet may be made of a single sheet or a combination of more than one sheet (e.g., multiple sheet sections that are joined together or coupled separately to the implant and/or a support structure). For example, a covering may be made from multiple sheets that each form a section of the covering (e.g., in much the same way as multiple pieces of fabric are sewn together to form an article of clothing).

According to some embodiments, one or more sheets forming a covering are coupled to the implant by attaching, adhesion or otherwise joining the one or more sheets to the implant or one or more components coupled to or arranged proximate the implant (e.g., a support structure coupled to or arranged proximate the implant). For example, one or more sheets forming a covering may be designed and reinforced by ties, strings or strips of material and/or may be glued to other structures or glued directly to the implant (or a portion of the implant) using, for example, biological glues, such as glues based on collagen, seaweed, or biological glues that change one or more properties under contact with materials like blood, water, etc., or exposed to and react to radiation, such as electromagnetic radiation such as UV, RF, laser, etc., or other types of radiation such as ultrasound. Such a covering may be coupled to a portion of the implant either pre-insertion into the biological anatomy (e.g., an annulus of an intervertebral disc) or coupled to the implant post-insertion. Alternatively, a covering may be coupled to a separate component and inserted separately from the implant, examples of which are discussed in further detail below.

Figure 3A:
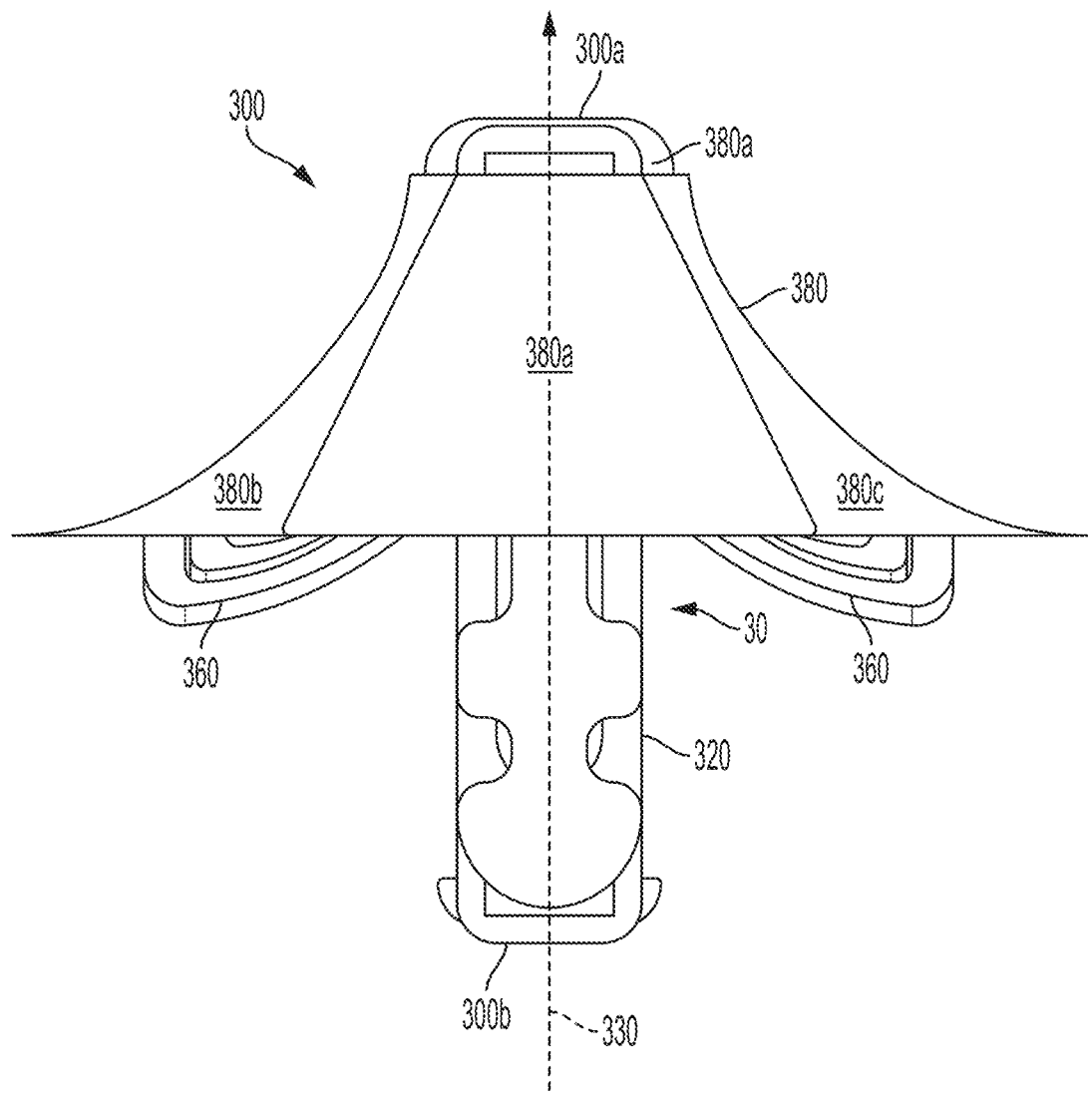
FIGS. 3A-3C illustrates a device comprising an implant and a covering open at a distal end and coupled to the implant, in accordance with some embodiments.
Figure 3B:
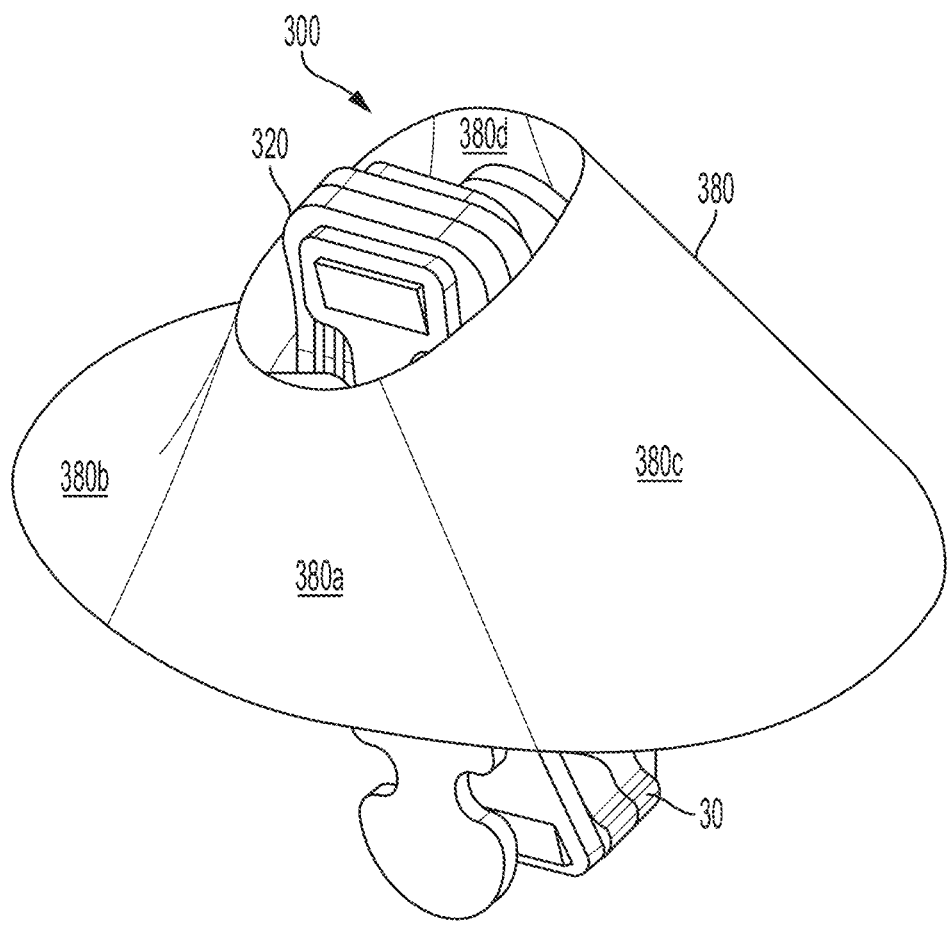
Figure 3C:
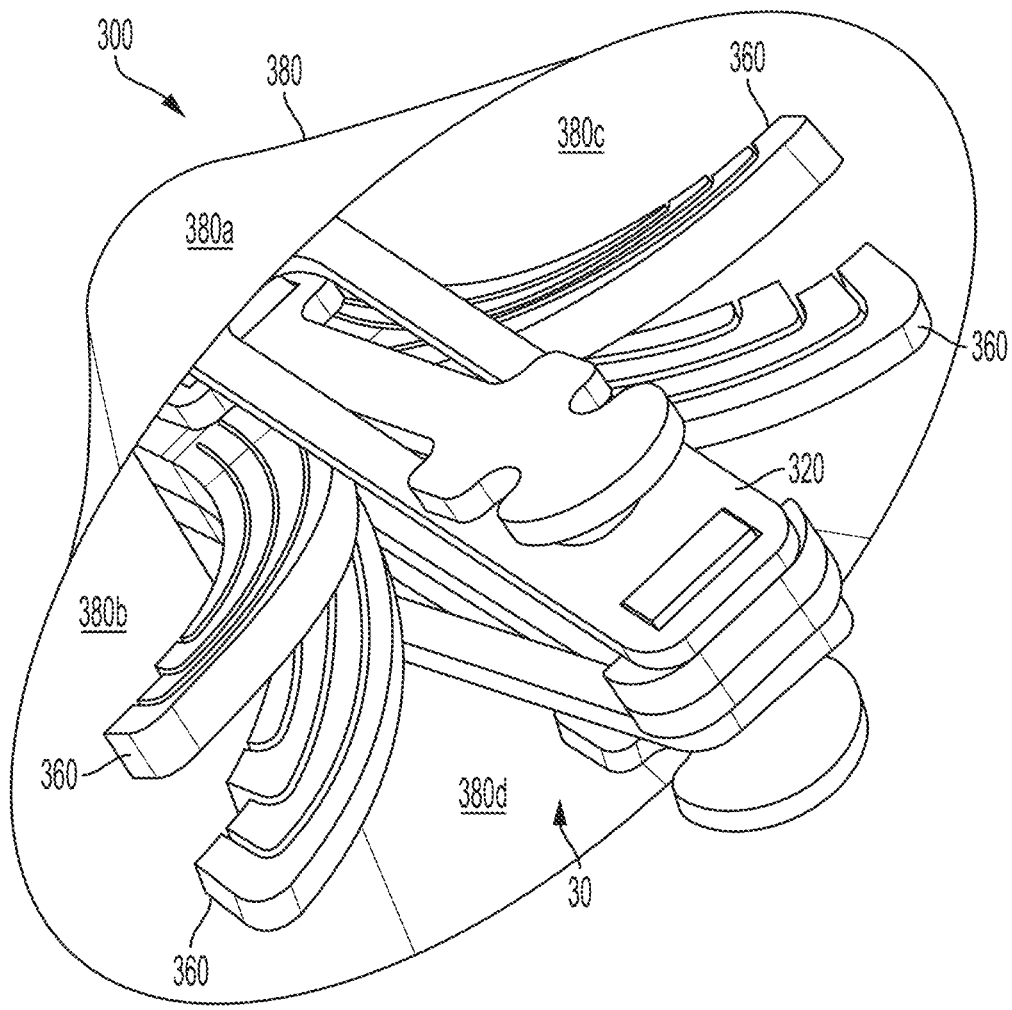

FIGS. 3A-3C illustrate an exemplary device 300 comprising an implant 30 (e.g., an implant that is similar or the same as implant 10 illustrated in FIGS. 1A-1C) and a covering 380 coupled to the implant (e.g., to one or more protrusions of the implant, to a body of the implant, or both). In the exemplary embodiment illustrated in FIGS. 3A-3C, covering 380 is arranged about a portion of implant 30 toward the distal end 300a of the implant. As discussed above, the terms "distal" and "proximal" are relative to the surgeon and so generally are also relative to the direction of insertion of the implant indicated by the direction of the arrow on axis 330. Accordingly, the distal side or distal end of an implant, covering or other object refers to the side that is further away from the surgeon and generally inserted first during implantation. Correspondingly, the proximal side or proximal end of an implant, covering or other object refers to the side that is closer to the surgeon and generally inserted last during implantation. Similarly, the terms "distally" and "proximally" refer herein to relative directions towards the respective ends of the implant relative to the surgeon and/or insertion direction.

Covering 380 may be coupled to body 320 and/or protrusions 360 that extend outward from body 320 (e.g., in a direction generally away from longitudinal axis 330). Covering 380 may be coupled to the implant using any suitable techniques, including by gluing (e.g., using any of the types of glues/adhesives discussed in the foregoing), tying, resting or fitting the covering on or to implant 30, or using any other suitable technique. For example, with respect to resting or fitting the covering on or to the implant, distal end 380a of covering 380 may be fabricated to fit snugly when coupled to the implant and/or configured to rest on the extended portions of protrusions 360 so that glues, ties or other techniques for attaching the covering are not needed. However, according to some embodiments, additionally or alternatively, one or more techniques for physically attaching the covering may be used (e.g., adhesives, ties, snaps, sockets, socks or envelops that encapsulate portions of the protrusions, etc.), as the aspects are not limited in this respect.

Covering 380 exhibits a generally frustoconical shape and is open at the distal end forming a "lamp shade" shaped configuration, as seen best from the view of the implant and covering shown in FIG. 3B. The opening may facilitate a tight fit to the implant by sizing the opening so that it fits over the distal end but is stopped by the increased dimensions of the implant formed, for example, where the body widens as a result of protrusions 360 beginning to extend away from the body. Covering 360 may partially or fully rest on protrusions 360, or it may be coupled to the implant without contacting the protrusions, as the aspects are not limited to any particular type of coupling.

A covering may be fabricated using a single piece of material (e.g., a single sheet), or may be fabricated using a plurality of section or pieces (e.g., a plurality of sheets) that are joined together (e.g., sewn, glued, fastened or otherwise affixed to each other) to produce the desired shape of the covering. For example, covering 380 may be formed from sheet sections 380a, 380b, 380c and 380d (visible in FIGS. 3B and 3C) that are portions of a single sheet of material (e.g., formed via a 3D printing process, patterned from a single piece of material, etc.), or one or more sections may be a separate sheet that are joined together. In the exemplary embodiment illustrated in FIGS. 3A-C, covering 380 exhibits a generally frustoconical or "lamp shade" shape. However, a covering coupled towards a distal end of an implant may take on any desired shape, as the aspects are not limited in this respect.

Figure 4C:
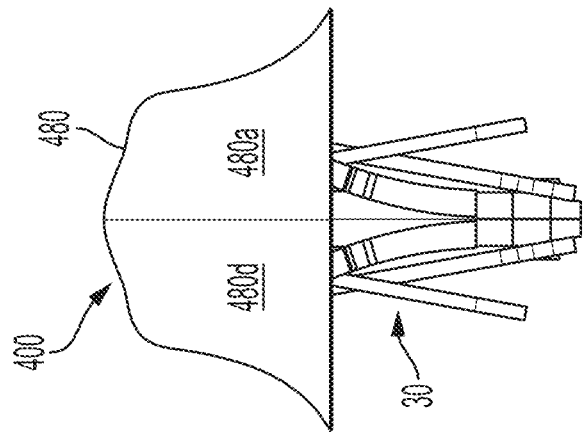
FIGS. 4A-4C illustrate a device comprising an implant and a covering closed at a proximal end and coupled to the implant, in accordance with some embodiments.
Figure 4B:
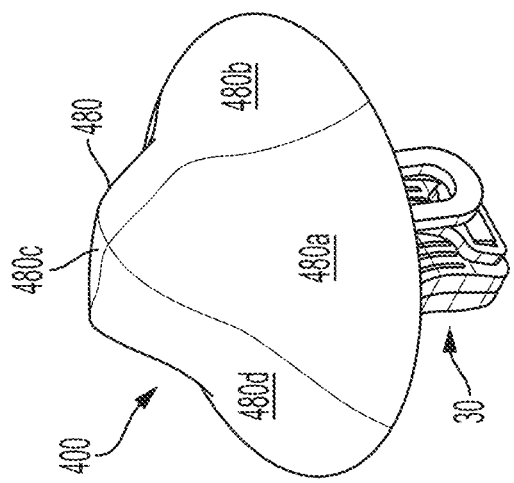
Figure 4A:
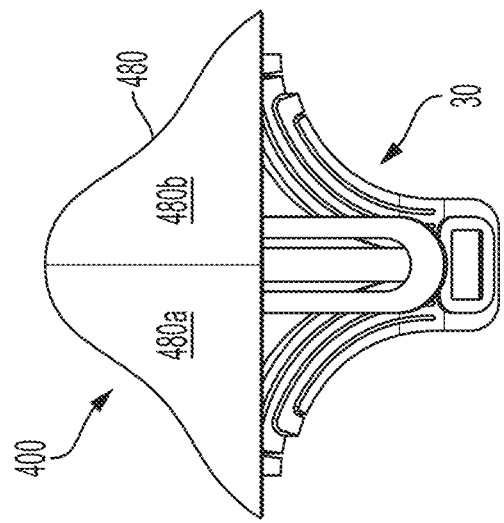

As shown, covering 480 is coupled towards the distal end of the implant. However, alternatively or additionally, a covering may be provided that is coupled towards a proximal end of the implant. In particular, FIGS. 4A-4C illustrate a device 400 comprising an exemplary implant 30 and a covering 480 coupled towards a proximal end of the implant, in accordance with some embodiments. Unlike the open form of covering 380 illustrated in FIGS. 3A-3C (e.g., a covering having an opening at the distal end), covering 480 is closed at the proximal end. In this configuration, covering forms a generally conical "hat" coupled towards the proximal end of implant 30 (e.g., fitted over or to the proximal side of the implant). Closed covering 480 may be fabricated using a single sheet of material or using a plurality of sheet sections that are joined to produce the desired shape. For example, in the exemplary embodiment illustrated in FIGS. 4A-4C, sheet sections 480a-d may be portions of a single sheet of material or may include separate sheets that are joined (e.g., via stitching, adhesive or other attachment means) to form the generally "pith helmet" shape exhibited by exemplar covering 480 that is coupled towards or to implant 30 using any suitable attachment technique. It should be appreciated that the shape of covering 480 is exemplary and a covering coupled towards a proximal end of an implant may having any desired shape, as the aspects of an implant may having any desired shape, as the aspects are not limited in this respect.

Figure 4F:
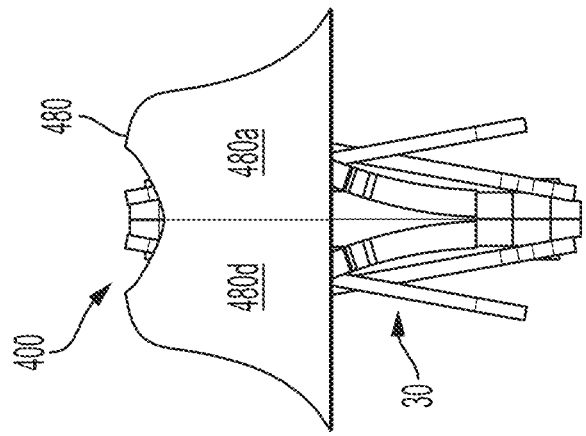
FIGS. 4D-4F illustrate a device comprising an implant and a covering open at a proximal end and coupled to the implant, in accordance with some embodiments.
Figure 4E:
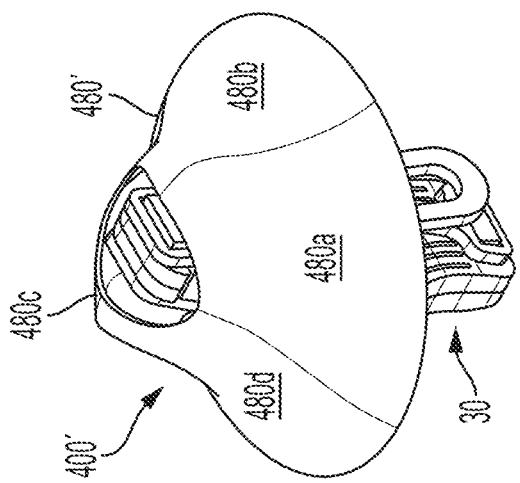
Figure 4D:
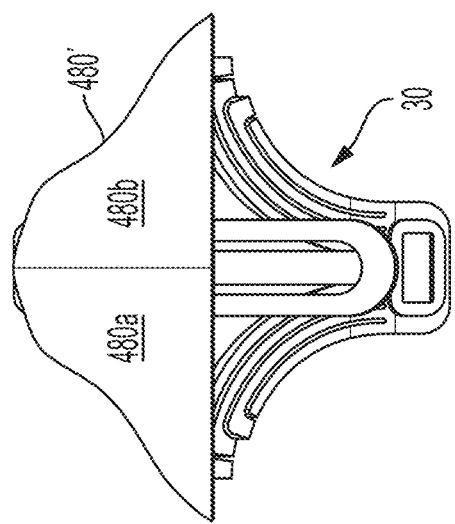

FIGS. 4D-4F illustrate a device 400' comprising an exemplary implant 30 and a covering 480' coupled towards a proximal end of the implant, in accordance with some embodiments. Covering 480' may be similar to covering 480 illustrated in FIGS. 4A-C in many respects. However, instead of being in closed form, covering 480' is open at the proximal end, as shown by the proximal end of implant 30 visible through the proximal opening of covering 480'. In this respect, the open form of covering 480' may be similar to that of covering 380 illustrated in FIGS. 3A-C, but covering 480' is instead coupled to a proximal end of the implant.

Figure 5:
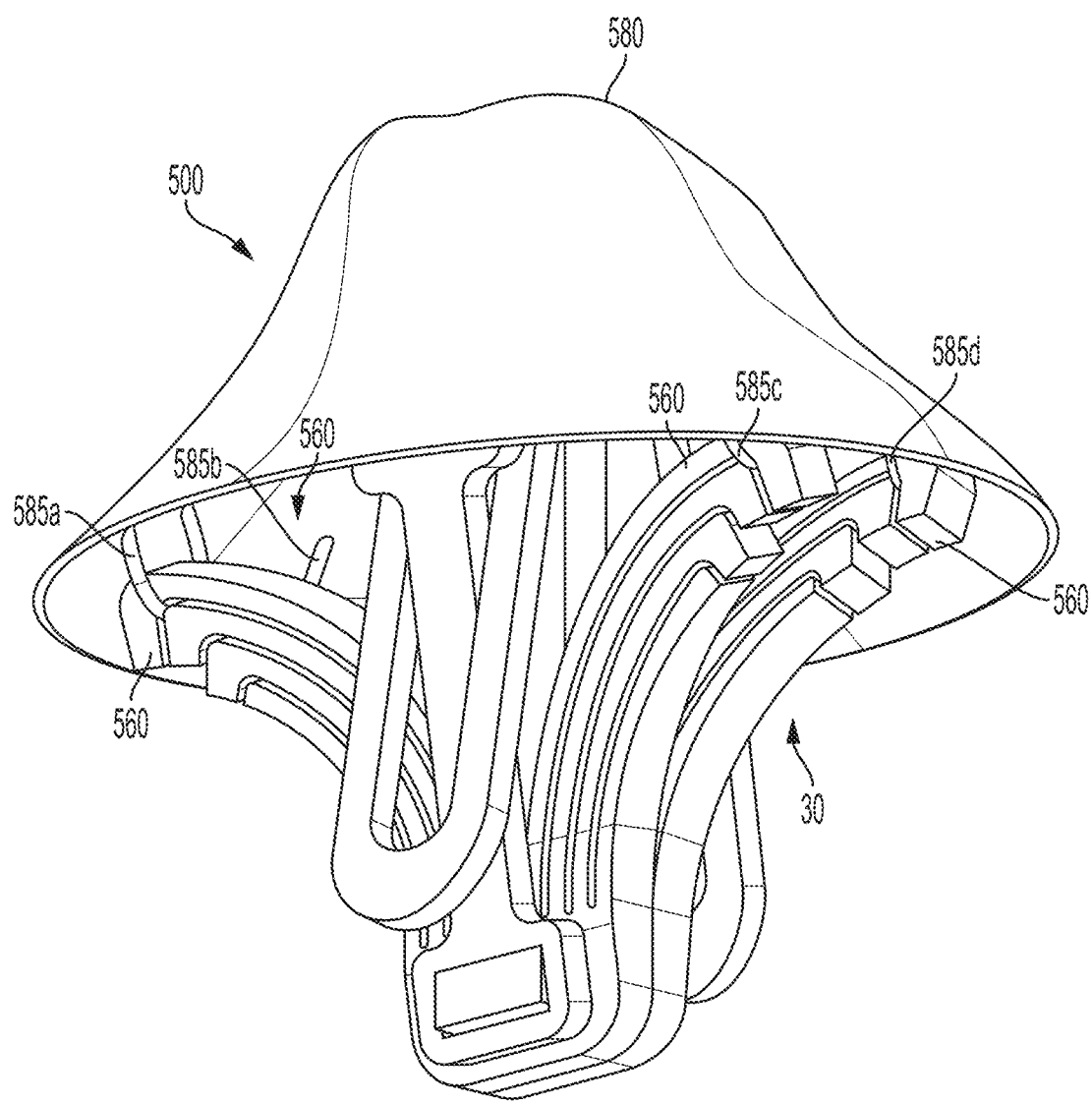
FIG. 5 illustrates a device comprising an implant and a covering coupled to the implant using ties, in accordance with some embodiments.

FIG. 5 illustrates a device 500 comprising an exemplary implant 30 and a covering 580 coupled to the implant using ties, in accordance with some embodiments. In particular, covering 580 is secured to protrusions 560 using ties 585 to couple the covering to implant 30. In the exemplary embodiment illustrated in FIG. 5, four ties 585a-c secure covering 580 to respective protrusions 560. However, in embodiments that utilize a tie, any number of ties may be used (e.g., a single tie, two ties, or any number of ties suitable for the design), as the aspects are not limited in this respect.

Ties 585 may be made from any material, including the same or different material as the covering and/or implant, and may be coupled to covering 580 in any suitable manner. For example, ties 585 may be formed by a stitch (e.g., thread that loops about the protrusion and is stitched to the covering), strap or other loop suitable for securing the covering. Ties 585 may alternately be secured to covering 580 using an adhesive, heat annealing (ironing), or other suitable technique, as the aspects are not limited in this respect. Covering 580 may be open (e.g., similar to covering 380 illustrated in FIGS. 3A-C), closed (e.g., similar to covering 480 illustrated in FIGS. 4A-C), or may take on any other configuration, further examples of which are described in detail below.

Figure 6A:
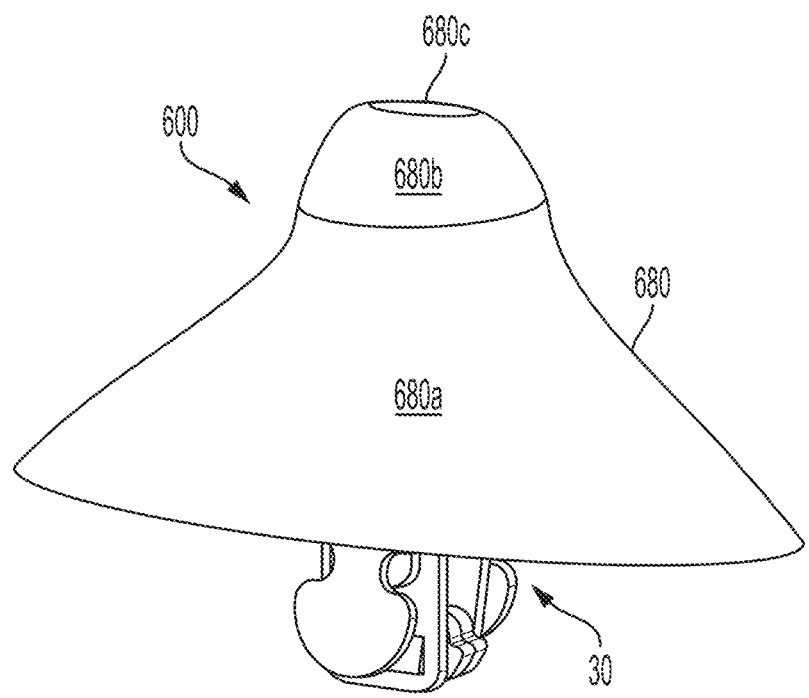
FIGS. 6A and 6B illustrate a device comprising an implant and a covering closed at a distal end coupled to the implant using ties, in accordance with some embodiments.
Figure 6B:
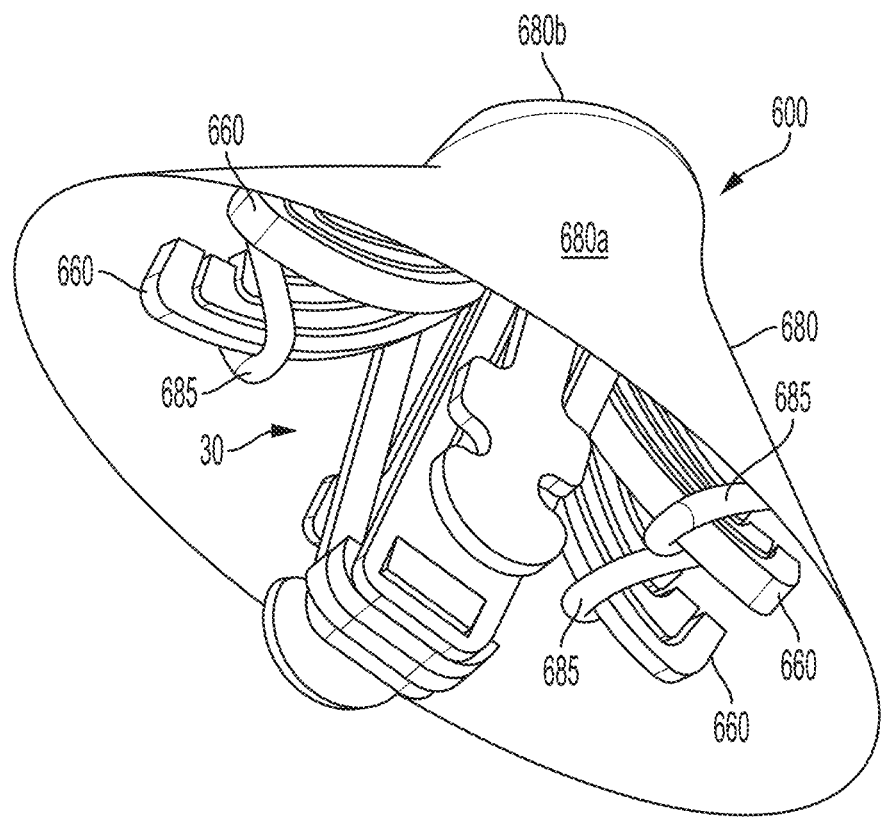

FIGS. 6A and 6B illustrate a device 600 comprising an implant and an exemplary closed covering coupled to the implant towards a distal end, in accordance with some embodiments. For example, implant 30 has a covering 680 coupled to protrusions 660 at least in part using ties 685, which may be coupled to covering 680 via any suitable technique, including the techniques described in connection with FIGS. 4A-4C. Closed covering 680 may be fabricated using a single sheet of material or using a plurality of sections that are joined to produce the desired shape. For example, in the exemplary embodiment illustrated in FIGS. 6A and 6B, sections 680*a-c* may be portions of a single sheet of material or may be separate sheets that are joined together (e.g., via stitching, adhesive or other attachment means) to form a generally conical "sun hat" shape that is coupled atop implant 30 using any suitable attachment technique.

In embodiments in which sections 680*a-c* are separate sheets that are joined together, the sheets may have concentric seams, as opposed to generally triangular sheet sections 480*a-d* that, embodiments where sections 480*a-d* are separate sheets, are joined at seams that run from the lower circumference of the covering at its proximal end and meet near or converge toward or at the distal end of the covering (though the covering may be preferably made substantially using a single sheet of material). Though covering 680 is illustrated in closed form (i.e., the covering is closed at the distal end of the covering), it should be appreciated that sheet section 680*c* and, alternatively, sheet section 680*b* may be eliminated, resulting in a covering in open form. For example, an open covering may be deployed by using just sheet 680*c*, which in such an embodiment would provide a covering using a single sheet of material. However, as discussed above, the entirety of the closed covering may be fabricated using a single sheet of material.

Accordingly, as illustrated by the exemplary devices 300, 400, 500 and 600 illustrated in FIGS. 3-6, a covering that fits on, over or is otherwise coupled towards a distal end of an implant can be configured in a varieties of ways to facilitate leakage protection and/or to assist in resisting displacement of the implant. According to some embodiments, covering 680 may be formed from a flexible material (e.g., a fabric, wire mesh, knitted fibers, or any other type of flexible material such as plastic, silicon, etc.) so as to not significantly inhibit the implants ability to flex under different stress, provide shock absorption and/or move according to the various degrees of freedom for which the implant is adapted.

Figure 7A:
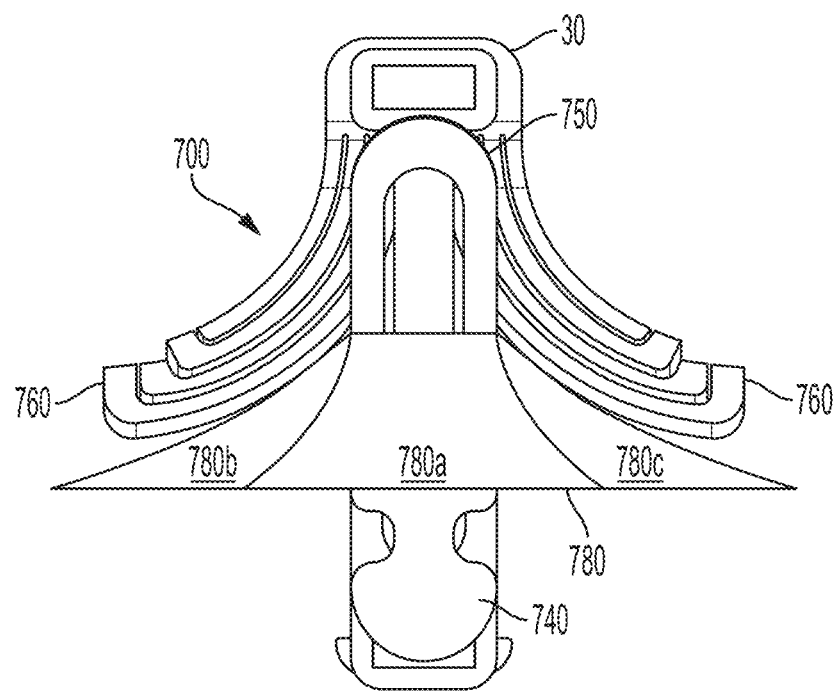
FIGS. 7A and 7B illustrate a device comprising an implant and a covering coupled towards the middle of the implant and extending in a direction towards a proximal end of the implant, in accordance with some embodiments.
Figure 7B:
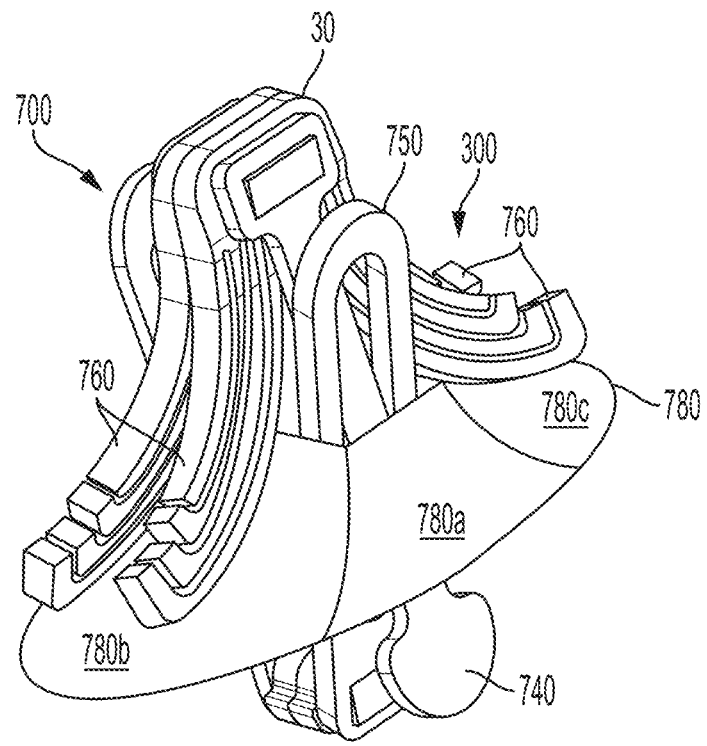

FIGS. 7A and 7B illustrate a device 700 comprising an implant and a covering coupled towards a proximal end of the implant. In particular, covering 780 is arranged about a portion of implant 30 toward the proximal end of the implant. For example, covering 780 may be coupled near the middle of the body of the implant (or at any other location) and extends toward the proximal end to form a "skirt" about the implant. Covering 780 may be coupled to protrusion(s) 740 and/or protrusion(s) 750 depending on where the covering is positioned along the body of the implant. Covering 780 may be coupled to protrusions by virtue of friction between the covering and the protrusion (or the implant body) at or near the opening at the distal end of the covering (e.g., by being restrained due to the size of the opening relative to the dimensions of the implant at that location).

Closed covering 780 may be fabricated using a single sheet of material or using a plurality of sheet sections that are joined to produce the desired shape (e.g., a frustoconical shape for the exemplary covering illustrated in FIGS. 7A and 7B). For example, in the exemplary embodiment illustrated in FIGS. 7A and 7B, sections 780*a-d* (780*a-c* of which are visible) may be portions of single sheet of material or may be separate sheets that are joined (e.g., via stitching, adhesive or other attachment means) to form a "skirt" shape about the implant that may be coupled near the middle of implant 30. The flair of the frustoconical shape determines the shape of the "skirt" (e.g., whether covering 780 is shaped more like a mini-skirt or a tutu).

Covering 780 may alternately be fabricated using a single sheet of material (e.g., a single section of material similar to sheet section 680*a* may be coupled near the middle of the implant) to form a generally seamless skirt about the implant. In embodiments in which the implant includes similar structures to implant 30, covering 780 may be coupled underneath or positioned proximally to protrusions 760 or similar structures, using any suitable attachment technique. It should be appreciated that a skirt shaped covering may be coupled anywhere along the body of the implant as desired, but is typically coupled near the middle of the body or more towards the proximal end of the implant.

Figure 8A:
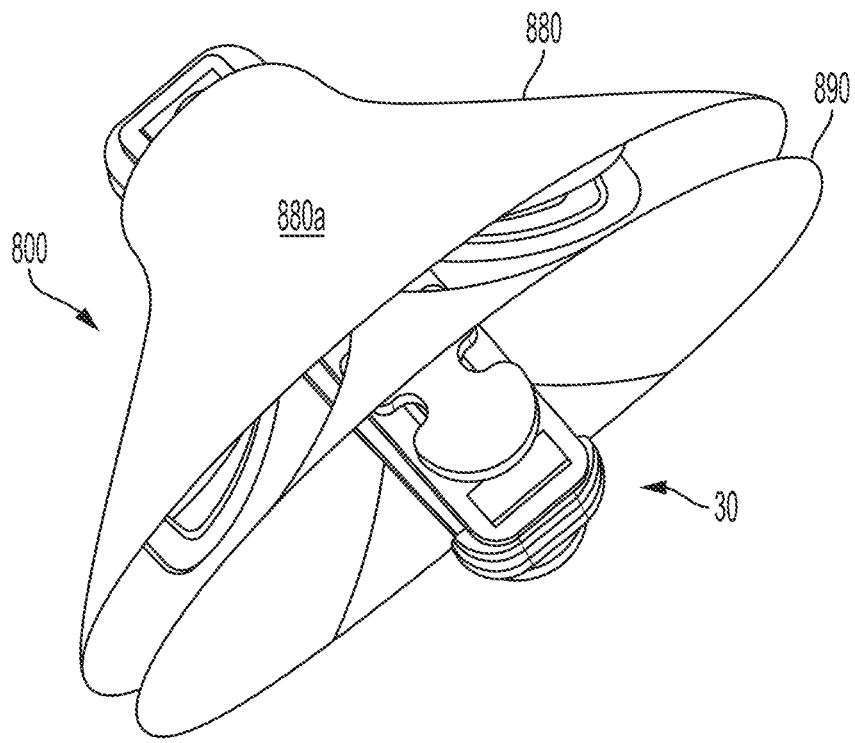
FIG. 8A illustrates a device comprising an implant, a first covering open at a distal end and coupled to the implant, and a second covering coupled towards the middle of the implant and extending in a direction towards a proximal end of the implant, in accordance with some embodiments.
Figure 8B:
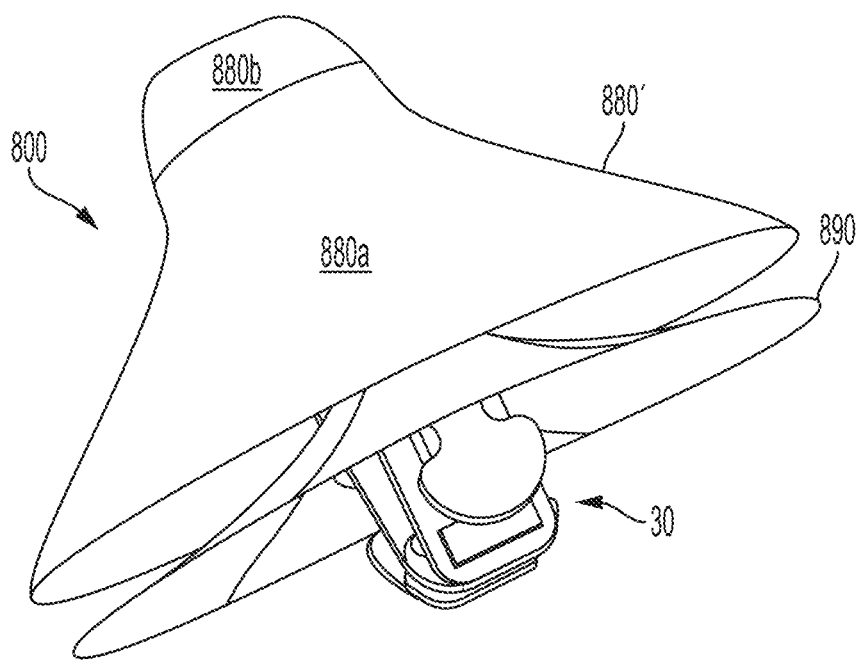
FIG. 8B illustrates a device comprising an implant, a first covering closed at a distal end and coupled to the implant, and a second covering coupled towards the middle of an implant and extending in a direction towards a proximal end of the implant, in accordance with some embodiments.

FIGS. 8A and 8B illustrate a device 800 comprising an implant 30, a first covering 880/880', and second covering 890 coupled to the implant. In the embodiment illustrated in FIGS. 8A and 8B, first covering 880 or '800 is coupled towards the distal end of implant 30 and second covering 890 is coupled proximally to first covering 880/880'. In FIG. 8A, first covering 880 is configured in open form (open at the distal end of the covering) and, in FIG. 8B, first covering 880' is configured in closed form (closed at the distal end of the covering). As shown, first covering 880 is formed from a single sheet of material, but may alternatively be formed using multiple sections (e.g., as illustrated by exemplary covering 380 illustrated in FIGS. 3A-3C). First covering 880/880' may include any of the features of coverings described herein and may be coupled to the implant using any suitable technique. Second covering 890 may be similar to covering 780 illustrated in FIGS. 7A and 7B and similarly may include any features of a covering described herein and may be coupled to the implant using any suitable technique.

Figure 9A:
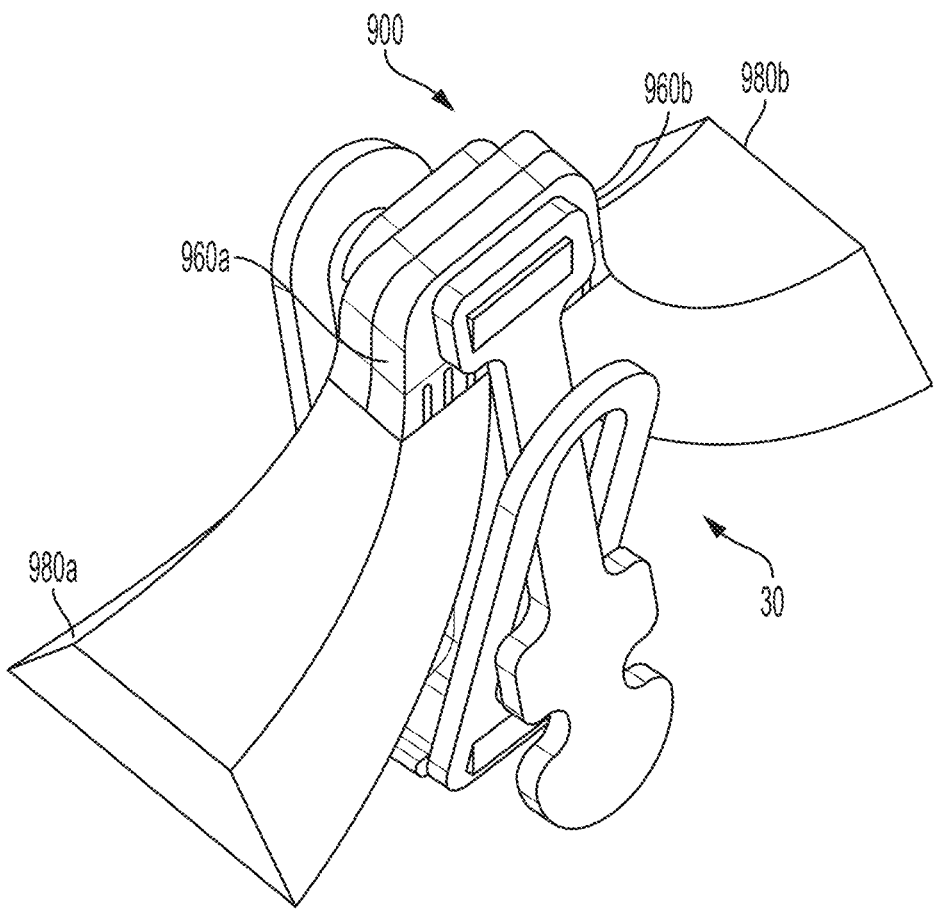
FIGS. 9A and 9B illustrate a device comprising an implant and coverings coupled to protrusions of the implant and provided in closed form to provide a sheath for respective protrusions.
Figure 9B:
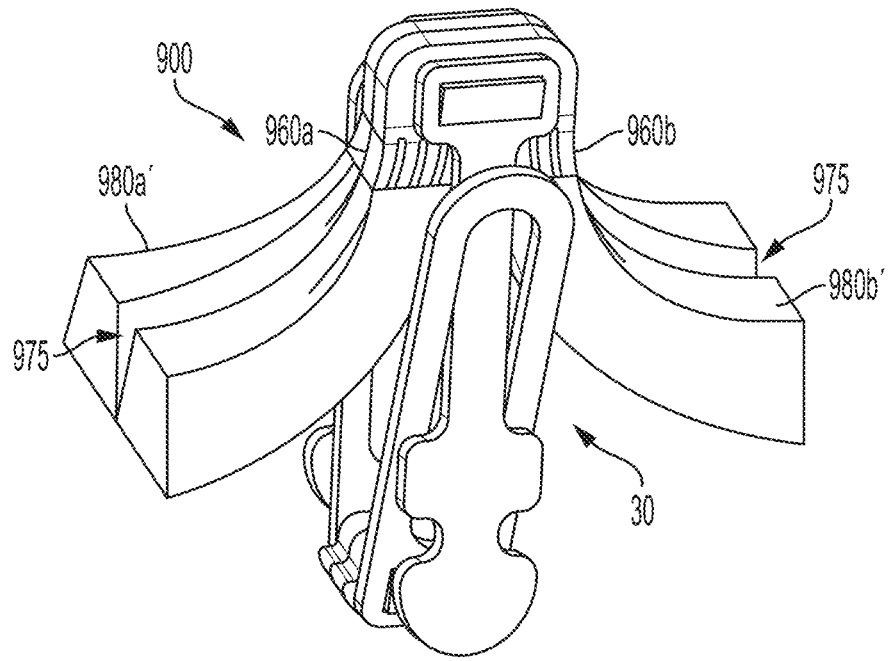
Figure 9C:
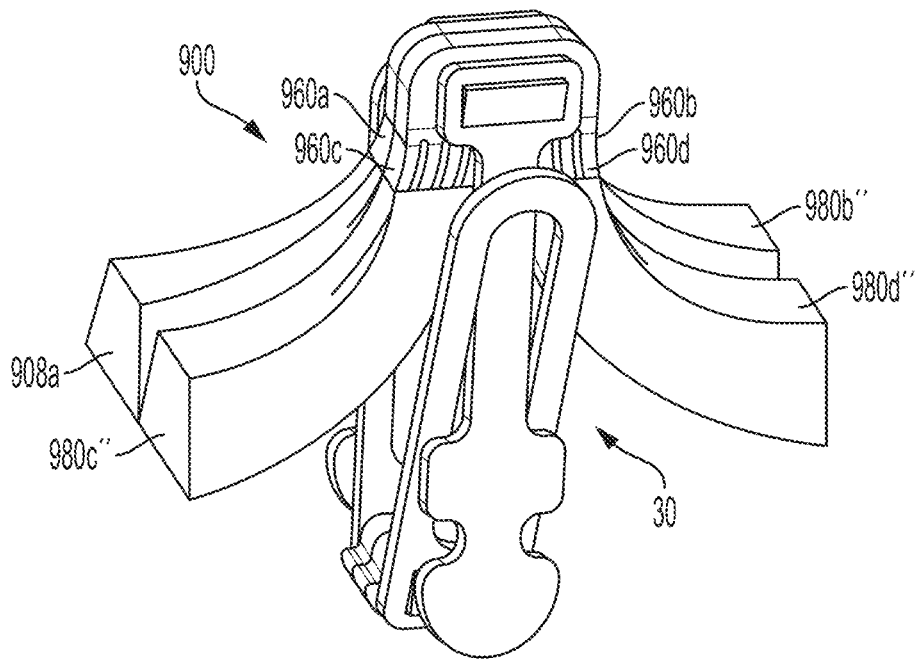
FIG. 9C illustrates a device comprising an implant and coverings coupled to protrusions of the implant and provided in closed form to provide a separate sheath for individual respective protrusions.

FIG. 9A illustrates a device 900 comprising an implant 30 having a plurality of protrusions fitted with respective coverings, in accordance with some embodiments. In the exemplary embodiment illustrated in FIG. 9, covering 980*a* is fitted to protrusions 960*a* and covering 980*b* is fitted to protrusions 960*b* to form a sheath over the respective protrusions. FIGS. 9B and 9C illustrate further embodiments of coverings configured to fit to one or more protrusions of the implant. In particular, FIG. 9B illustrates coverings 980*a'* and 980*b'* that, like the embodiment illustrated in FIG. 9A, each cover a respective pair of protrusions. However, coverings 980*a'* and 980*b'* are closer fit to the contours of the protrusions, particularly with respect to the space between adjacent protrusions where the covering is shaped to the form of a respective one of the pairs of protrusions, producing the V-shaped space or gaps 975 labeled in FIG. 9B.

By contrast, in the embodiment illustrated FIG. 9C, each of four protrusions is fitted with a respective separate covering. In particular, covering 980*a"* is fitted to protrusion 960*a*, covering 980*b"* is fitted to protrusion 960*b*, covering 980*c"* is fitted to protrusion 960*c* and covering 980*d"* is fitted to protrusion 960*d*. Accordingly, coverings configured to cover one or more protrusions (e.g., as a sheath) may be fitted to separate individual protrusions or may be fitted to more than protrusion, as the aspects are not limited in this respect. Coverings 980 may be configured in closed form at the end of the protrusion, like the sheath coverings illustrated in FIGS. 9A-C, or may be configured in open form at the end of the protrusion to form a sleeve, either for individual protrusions, pairs of protrusions or other groups of protrusions, as the aspects are not limited in this respect.

Figure 10A:
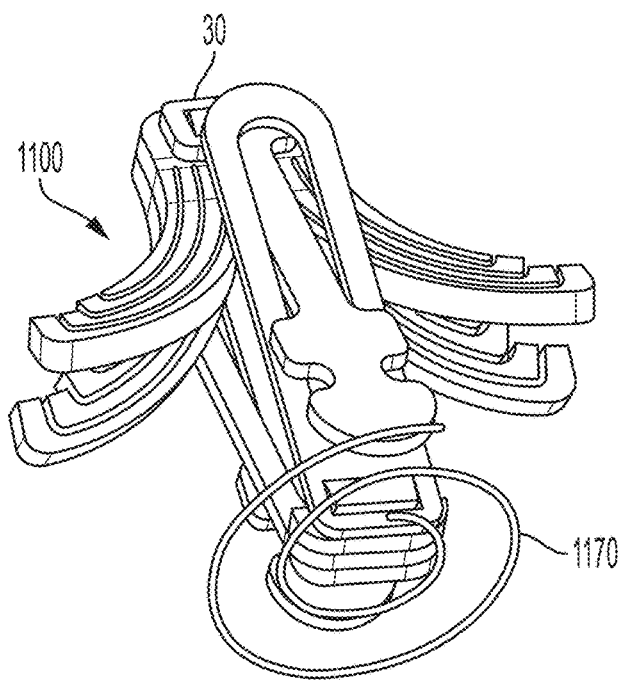
FIGS. 10A and 10B illustrate a device comprising an implant and a coil support structure coupled to a proximal end of the implant, in accordance with some embodiments.
Figure 10B:
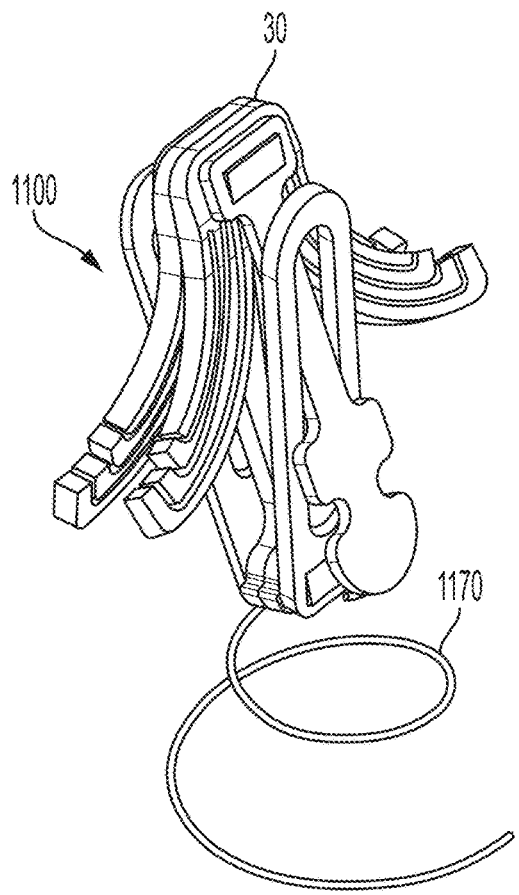

In the above exemplary embodiments of coverings, the one or more sheets, membranes, skins, etc., forming a covering are generally coupled directly to the implant or a portion of the implant. In other embodiments, one or more coverings may be indirectly coupled to an implant via a direct coupling to a support structure that is then, in turn, directly coupled to the implant, some examples of which are discussed in further detail below. For example, FIGS. 10A and 10B illustrate a device 1100 comprising an implant and a support structure 1170 in the shape of a coil (e.g., a helicoil) coupled to the implant. In particular, support structure 1170 may be formed in the shape of a spiral and coupled to a proximal end of the implant 30. Coil 1170 may be configured in any desired geometric shape such as cylindrical, conical, helical or any other suitable geometry, as the aspects are not limited for use with a support structure of any particular geometric shape. Coil 1170 is configured to assist in sealing, for example, a defect or fracture in an annulus of an intervertebral disc, in accordance with some embodiments.

FIG. 10A illustrates device 1100 in a closed configuration with the coil compressed and brought in close to the implant to facilitate insertion of the device into biological anatomy. FIG. 10B illustrates device 1100 in an open configuration in which the coil has been expanded outward to facilitate leakage prevention and/or to resist implant displacement after the device has been deployed.

Figure 11:
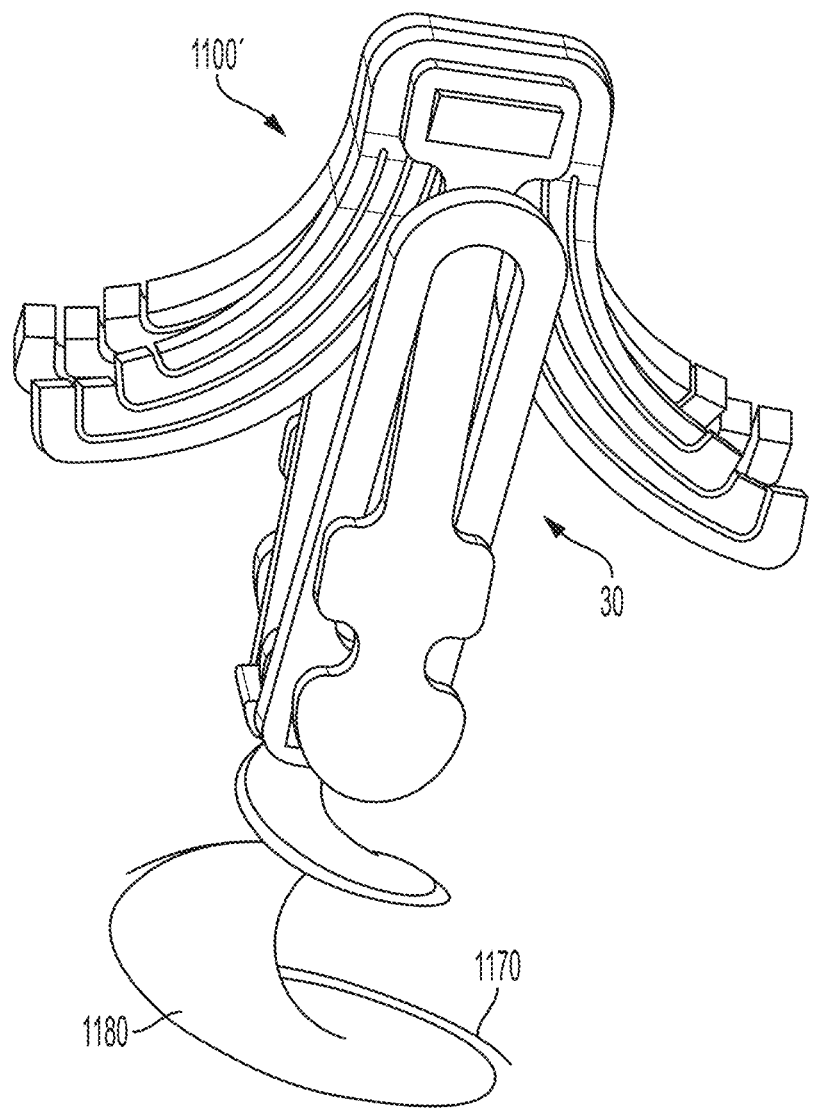
FIG. 11 illustrates a device comprising an implant and a covering indirectly coupled to the implant via a coil support structure coupled to the implant, in accordance with some embodiments.

Coil 1170 may be deployed as illustrated in FIGS. 10A and 10B, or may alternatively have a covering coupled to the coil to facilitate leakage prevention and to assist is resisting displacement of the implant, in accordance with some embodiments. For example, a covering 1180 may be coupled to a coil 1170 as in device 1100' illustrated in FIG. 11. It should be appreciated that any of the coverings discussed herein may be used alone or in any combination, as the aspects are not limited in this respect. For example, covering 1180 may be used alone or in combination with any of the coverings that are coupled to the body of the implant, one or more protrusion of the implant and/or any other portion of the implant, as described in the foregoing.

Figure 12A:
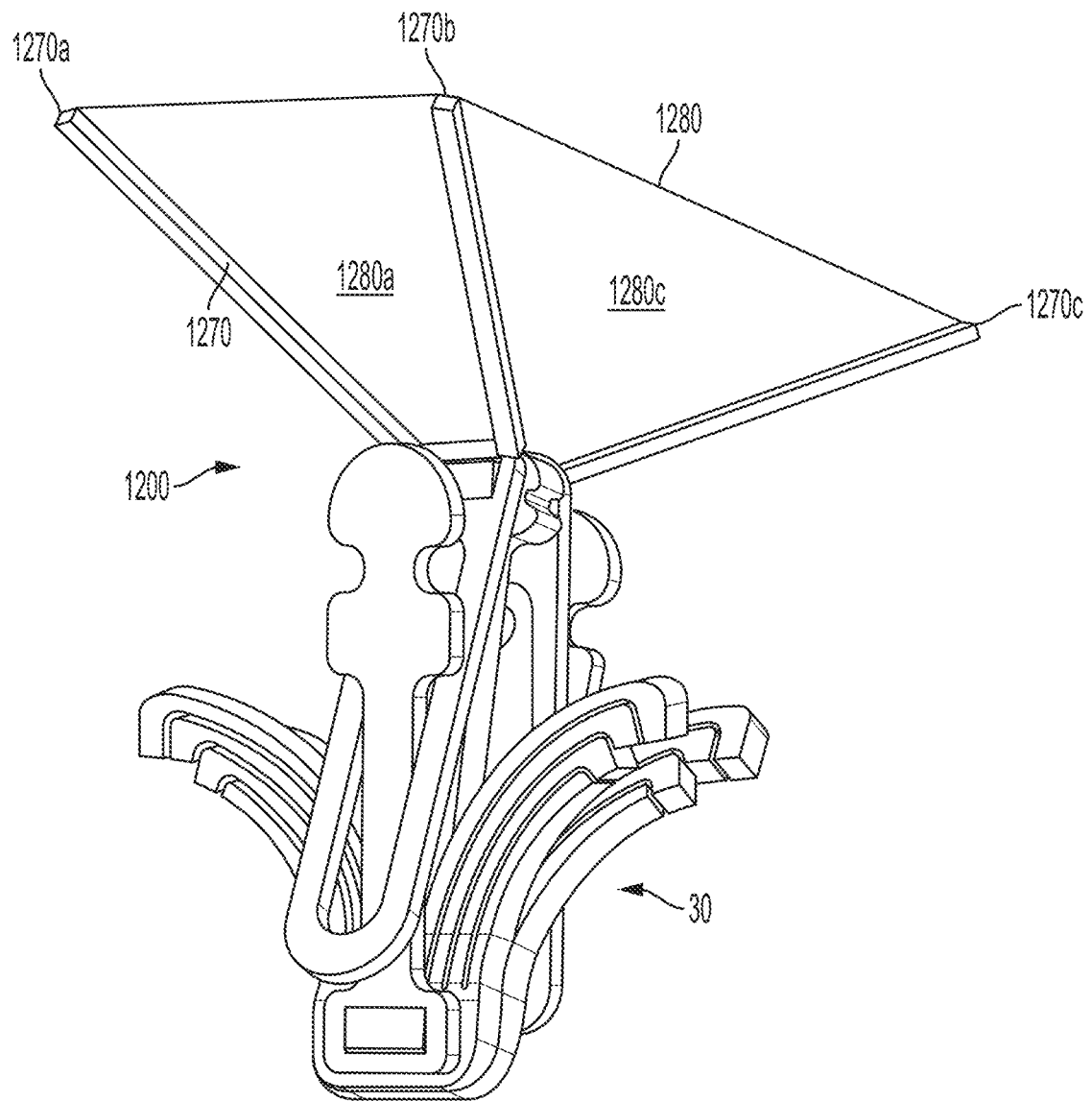
FIG. 12A illustrates a device comprising an implant and a covering indirectly coupled to the implant via a support structure in an open configuration, in accordance with some embodiments.
Figure 12B:
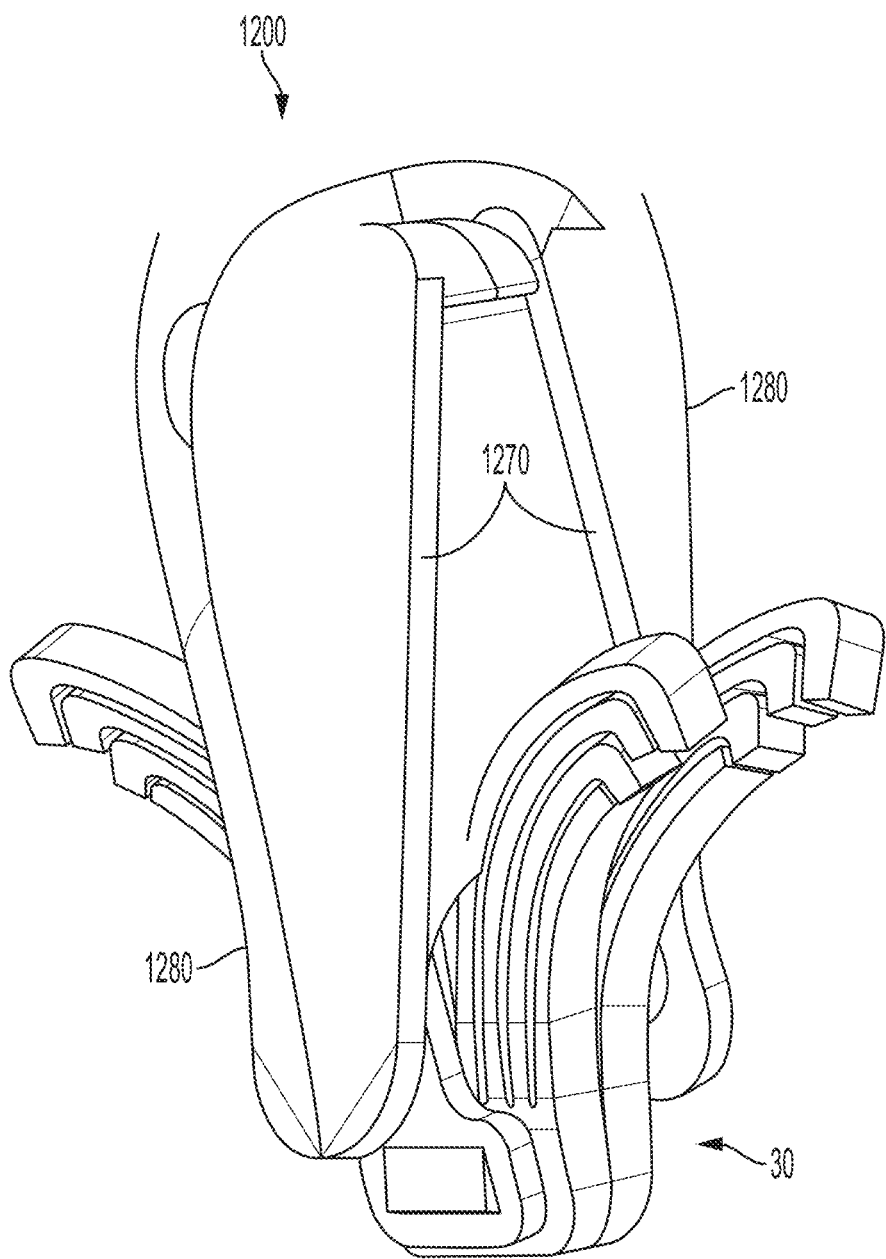
FIG. 12B illustrates the device of FIG. 12A in a closed configuration, in accordance with some embodiments.

FIGS. 12A and 12B illustrate a device 1200 comprising an implant, a support structure and a covering coupled to the support structure in the open/deployed configuration and the closed/insertion configuration, respectively. As shown in FIG. 12A, a support structure 1270 is coupled to a proximal end of an implant 30 and a covering 1280 is coupled to support structure 1270. Support structure 1270 comprises a plurality of ribs (e.g., ribs 1270a, 1270b and 1270c visible in FIG. 12) configured to support covering 1280. For example, covering 1280 may comprise a plurality of sheets or sheet sections (e.g., sheet sections 1280a, 1280b and 1280c visible in FIG. 12) that are coupled between the ribs of support apparatus 1270. Support structure may be configured so that it can be opened and closed like an umbrella to transition between an insertion configuration and a deployed configuration, as shown in FIG. 12B wherein support structure 1270 is folded down close to the body of the implant. It should be appreciated that support structure 1270 (or other support structure) may alternatively or additionally be coupled to the distal end of an implant, as the aspects are not limited in this respects.

Figure 13B:
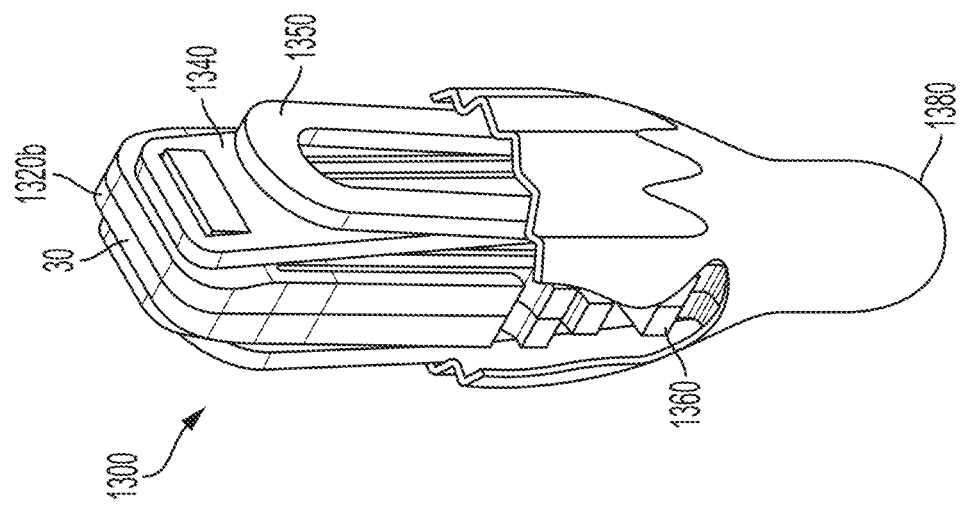
FIG. 13B illustrates a device comprising the implant of FIG. 13A and a covering in a closed or insertion configuration and coupled to the implant, in accordance with some embodiments.
Figure 13A:
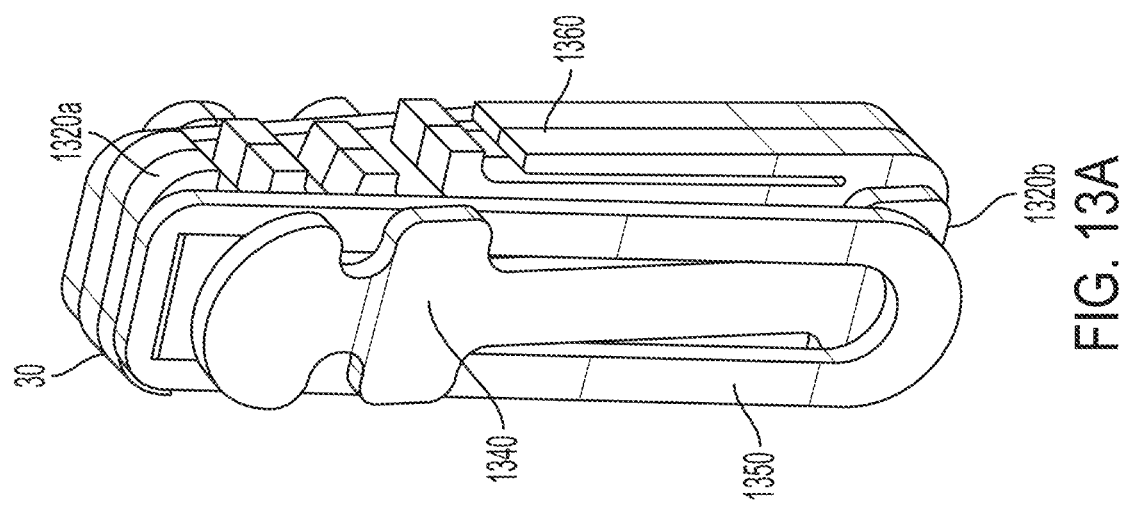
FIG. 13A illustrates an implant in a closed or insertion configuration.

As discussed above, an implant may be configurable between an insertion configuration (e.g., as illustrated in FIG. 1C) suitable for insertion into biological anatomy (e.g., via a defect in the annulus of a vertebral disc to be sealed by the implant) and a deployed configuration (e.g., as illustrated in FIGS. 1A, 1B, FIG. 2, etc.). FIG. 13A illustrates an implant 30 configured in an insertion configuration (e.g., in a configuration similar to or the same as the insertion configuration illustrated in FIG. 1C) in which protrusions 1340, 1350 and 1360 are configured in a position close in towards body 1320 in preparation for insertion. FIG. 13B illustrates a device 1300 in which a covering also configured in an insertion or closed position to facilitate insertion is coupled to implant 30.

In particular, covering 1380 is configured in an insertion configuration and coupled to implant 30 at a proximal end of the implant in preparation for insertion of device 1330 (i.e., simultaneous insertion of the implant and the covering coupled thereto). For example, covering 1380 may be similar to or the same as covering 480 illustrated in FIGS. 4A-4C. It should be appreciated that covering 1380 may alternatively be in open form like covering 480' illustrated in FIGS. 4D-F. Furthermore, according to some embodiments, covering 1380 may be coupled to the distal end of the implant in either open or closed form (e.g., similar to or the same as covering 380 illustrated in FIGS. 3A-3C or covering 680 illustrated in FIGS. 6A and 6B, respectively). In this configuration, the delivery system illustrated in FIG. 3A-3D of the incorporated '263 PCT Application and discussed in the accompanying description can be used to assist a surgeon in inserting device 1300 comprising implant 30 and covering 1380 into, for example, a herniated disc to facilitate sealing a defect of the disc annulus.

Figure 14A:
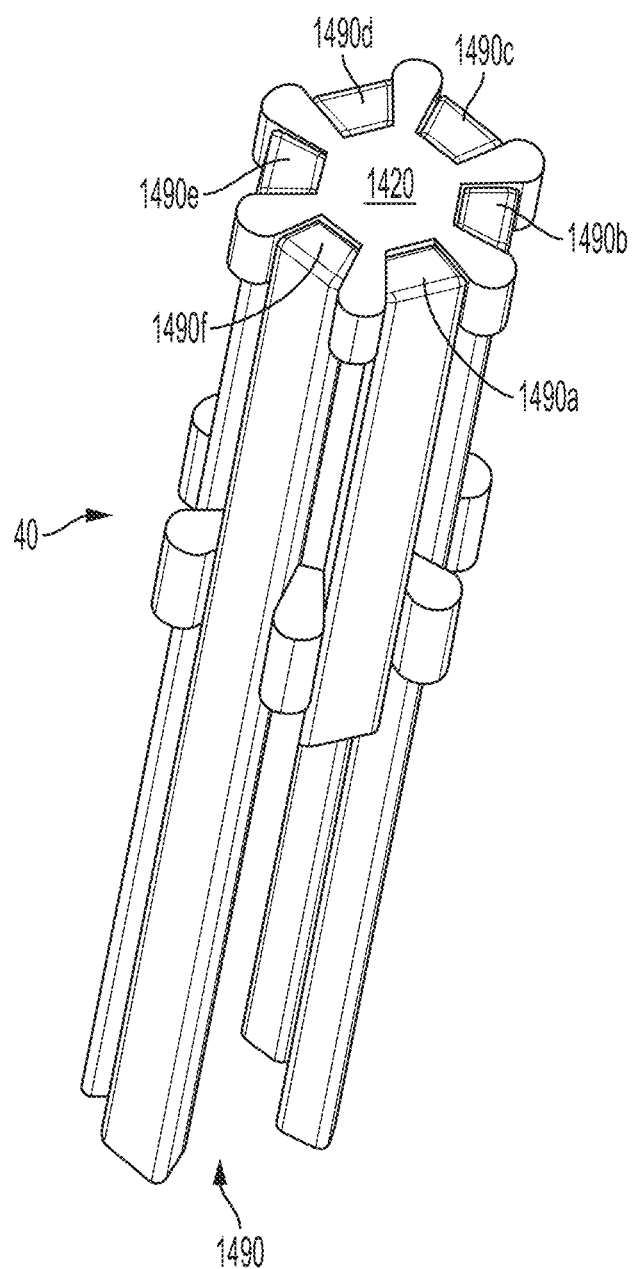
FIG. 14A illustrates an implant in a closed or insertion configuration, in accordance with some embodiments.

FIGS. 14A-14E illustrate an implant 40, in accordance with some embodiments. In FIG. 14A, implant 40 is shown in its insertion or closed configuration and in FIGS. 14B and 14C, implant 40 is illustrated in its deployed or open configuration. Implant 40 comprises a body 1420 about which a plurality of protrusions 1490 are arranged at a distal end of the body. In particular, protrusions 1490a-e are coupled to body 1420 at a distal portion 1420a of the body via a hinge or joint that allow each protrusion to pivot from the insertion configuration illustrated in FIG. 14A to the deployed position illustrated in FIGS. 14B and 14C. In this embodiment, protrusions 1490 are configured as arms that, when deployed, rest on the inner side of an annulus to facilitate leakage and implant displacement prevention. In the deployed configuration, each protruding arm 1490 extends radially outward from the distal end (distal portion 1420a) of body 1420 in a manner similar to the blades of a helicopter (or the ribs of a umbrella). For exemplary implant 40, protrusions around provided around the circumference of the distal portion 1420a of body 1420.

Figure 14B:
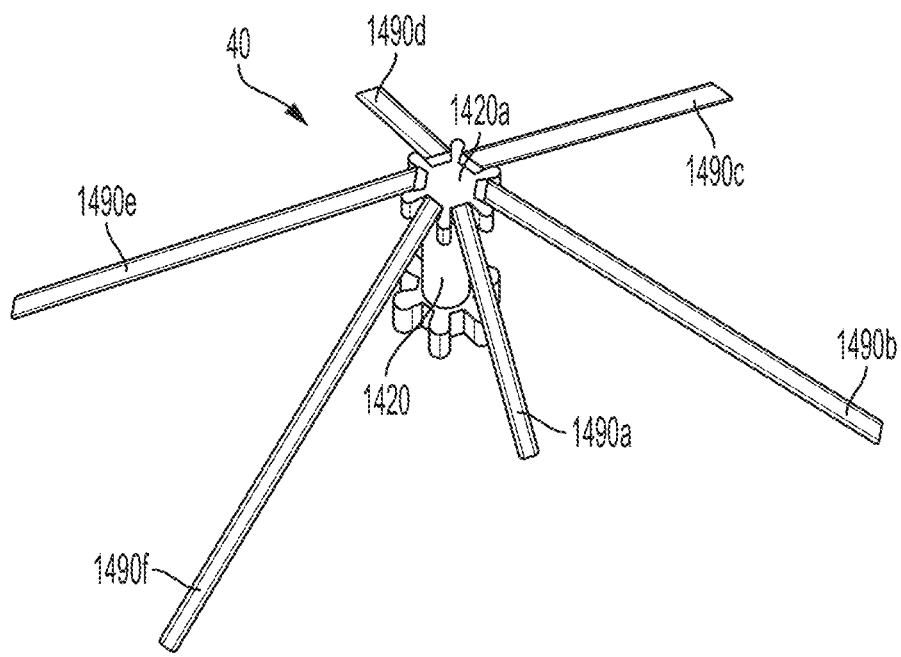
FIGS. 14B and 14C illustrate the implant illustrated in FIG. 14A in an open or deployed configuration, in accordance with some embodiments.
Figure 14C:
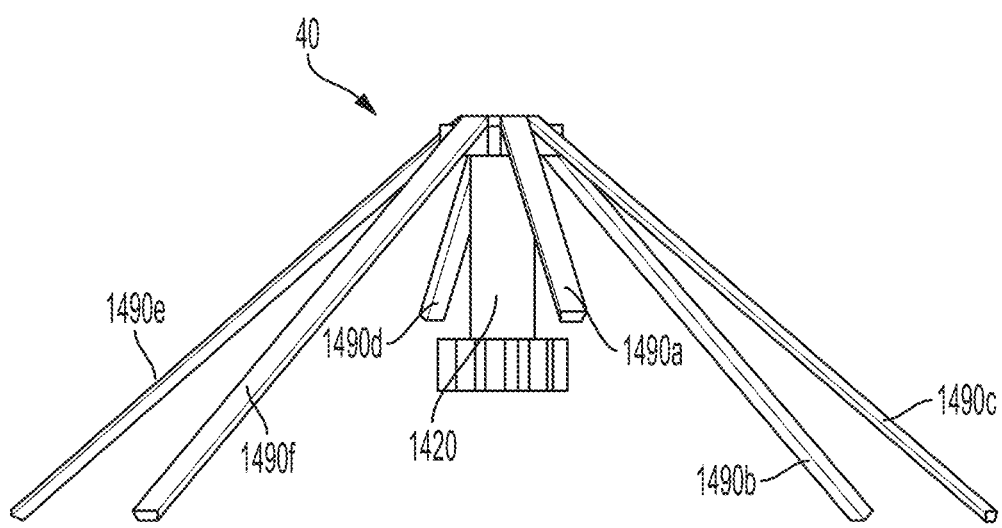
Figure 14D:
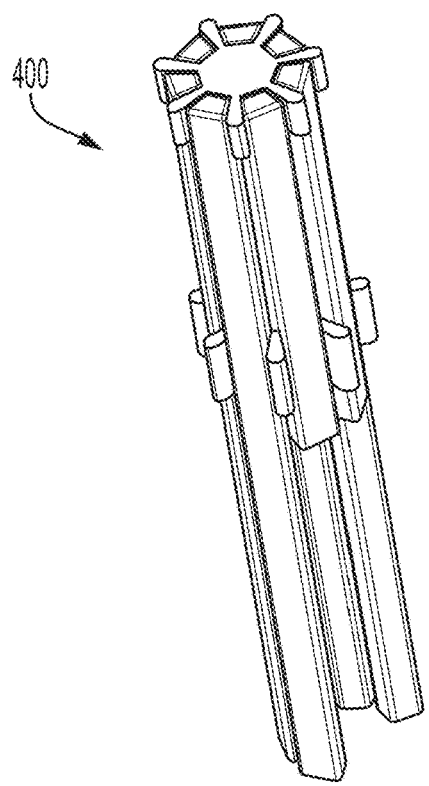
FIG. 14D illustrates an implant in a closed or insertion configuration, in accordance with some embodiments.
Figure 14E:
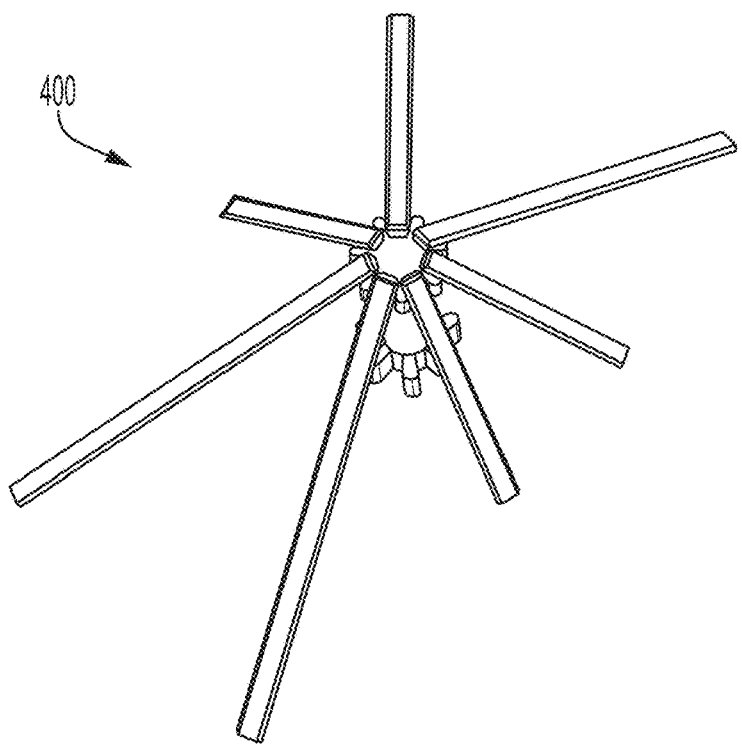
FIG. 14E illustrates the implant illustrated in FIG. 14D in an open or deployed configuration, in accordance with some embodiments.

According to some embodiments, at least one protrusion 1490 has a different length than at least one other protrusion, as shown by the varying lengths of the protrusions in the exemplary implant illustrated in FIGS. 14A-C. However, each protrusion 1490 may have the same length, as the aspects are not limited in this respect. Implant 40 may include any number of protrusions extending from the distal portion 1420a of central body 1420 (e.g., between 2 and 10 arms, and may include an even or odd number of arms, etc.). For example, exemplary implant 40 illustrated in FIGS. 14A-C comprises six protrusions while exemplary implant 40 illustrated in FIGS. 14D and 14E comprises seven protrusions. However, any suitable number of protrusions (e.g., protrusions connected via hinges or joints and configurable to extend radially outwards from a distal end of the body of an implant) that provide desired levels of leakage and/or implant displacement prevention may be used, as the aspects are not limited for use with any particular number of protrusions. Alternatively or additionally, protrusions 1490 may be provided on the proximal end of body 1420 via the same hinge mechanism illustrated on the distal end of the body, as the aspects are not limited in this respect.

Figure 15C:
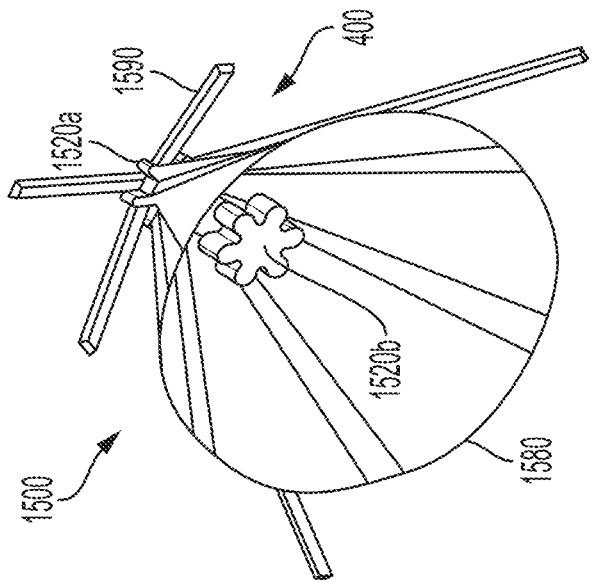
FIGS. 15B and 15C illustrate the device illustrate in FIG. 15A in an open or deployed configuration, in accordance with some embodiments.
Figure 15B:
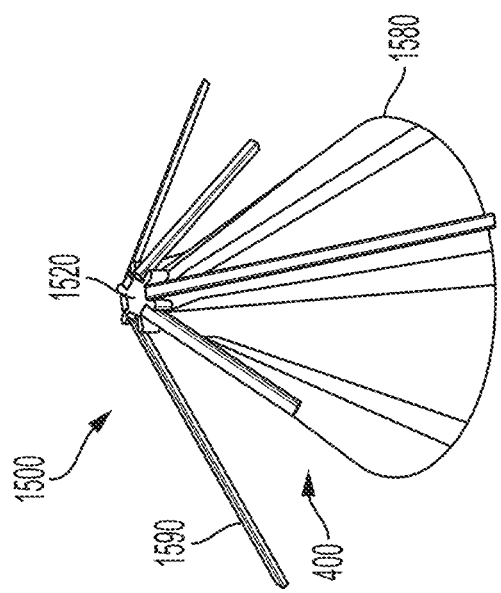
Figure 15A:
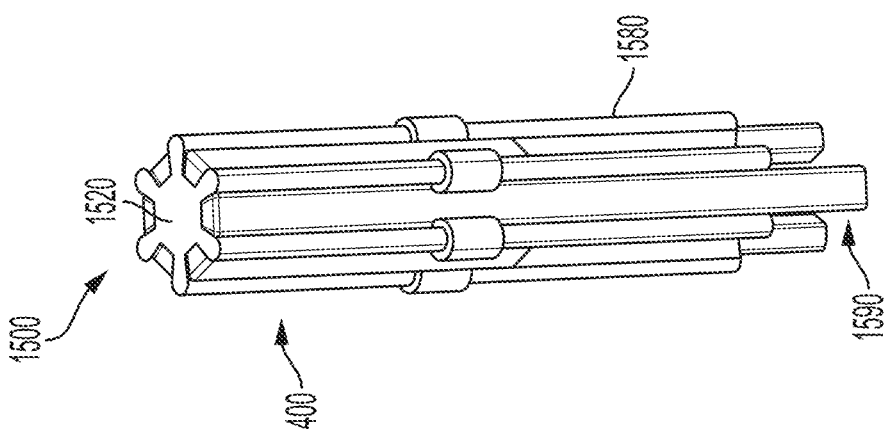
FIG. 15A illustrates a device comprising an implant and a covering coupled thereto in a closed or insertion configuration, in accordance with some embodiments.

According to some embodiments, a covering may be coupled to an implant similar to or the same as implant 40 illustrated in FIGS. 14A-E to facilitate improved leakage and/or implant displacement prevention. For example, FIGS. 15A-C illustrate a device 1500 comprising an implant 40 and covering 1580 coupled to the implant, in accordance with some embodiments. FIG. 15A illustrates device 1500 configured in an insertion configuration in which protrusions 1590 and covering 1580 are positioned close to body 1520 to facilitate insertion of the device. FIGS. 15B and 15C illustrate device 1500 in a deployed configuration in which protrusions 1590 and covering 1580 extend outward from body 1520. Covering 1580 may be, for example, coupled to distal end 1520a of body 1520, as shown in FIGS. 15A-C. Alternatively, covering 1580 may be coupled to protrusions 1590 so that the extension of protrusions 1590 during deployment also deploys covering 1580. Covering 1580 may be coupled to implant 40 in other ways and at other locations, as the aspects are not limited in this respect.

FIGS. 16A and 16B illustrate an exemplary implant in accordance with further embodiments. Implant 600 may be similar to implant 40 in that a body of the implant is configured at its distal end to accommodate a plurality of protrusions that are pivotally connected to the body so as to be able to configured between an insertion configuration in which the protrusions are positioned close to the body and a deployed configuration in which the protrusions are expanded outward so that they extend radially from the distal end of the body, several embodiments of which were described in connection with FIGS. 14 and 15. Implant 600 differs in that the implant has a body 1620 comprising a hollow cylindrical portion 1620b through which a plurality of strands 1622 extend outward from the proximal end (e.g., strands 1622a-1622e illustrated in FIGS. 16A and 16B). Strands 1622 may be formed according to any geometry (e.g., cylindrical tubes, strips, or strands of others geometries) and are generally flexible so as to make contact with the walls of an insertion corridor (e.g., an annulus defect) to create friction to facilitate leakage protection and/or implant displacement prevention.

For example, when the implant is in a closed configuration during insertion, protrusions 1690 and strands 1622 are configured to allow the implant to be moved in the insertion direction with as little resistance as possible. After the implant has been inserted and configured in its open position, protrusions 1690 and strands 1622 resist movement in the opposite direction by providing an anchor (protrusions 1690) against the inner wall of the annulus cavity and by providing contact friction (strands 1622) with the inner wall of the insertion corridor (e.g., annulus defect), respectively, as discussed in further detail in connection with FIGS. 18-21.

FIG. 17 illustrates a variation of the exemplary implant described in connection with FIGS. 16A and 16B. In particular, implant 700 has a body 1720 consisting essentially of the distal portion that accommodates the configurable protrusions 1790. Strands 1722 are coupled to body 1720 (which is disc-shaped) and extend downward towards the proximal end of the implant. In the exemplary embodiment illustrated in FIG. 17, the cylindrical portion of the body (e.g., cylindrical portion 1620 illustrated in FIGS. 16A-C) has been eliminated. A covering may be coupled to any of the exemplary implants illustrated in FIGS. 16A-C and 17 in the same or similar manner illustrated in FIGS. 15A-C and described in the accompanying description to facilitate improved leakage protection and/or implant displacement prevention.

Figure 18A:
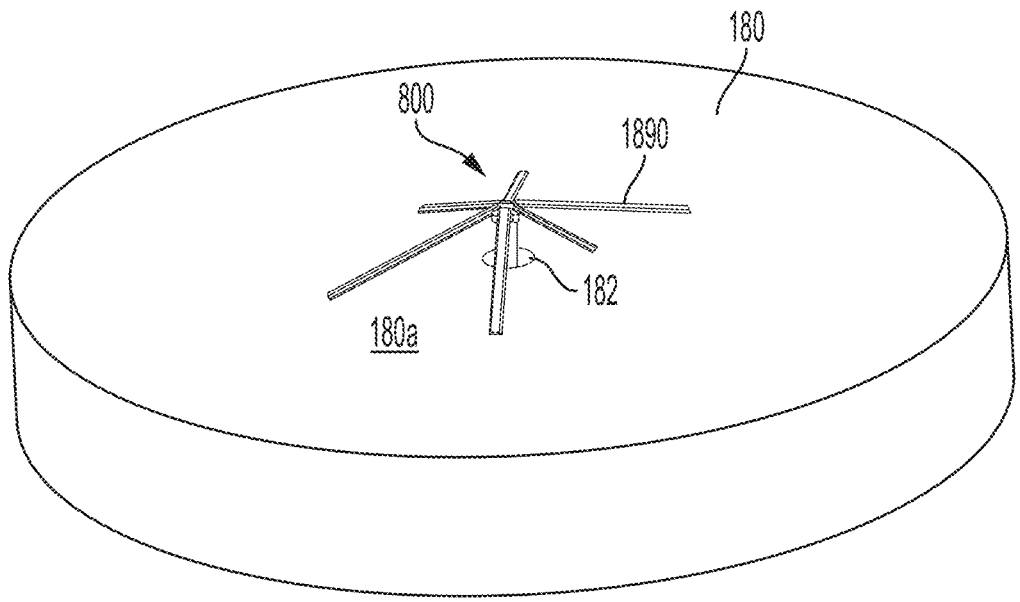
FIGS. 18A and 18B illustrate an implant deployed in connection with biological anatomy, in accordance with some embodiments.
Figure 18B:
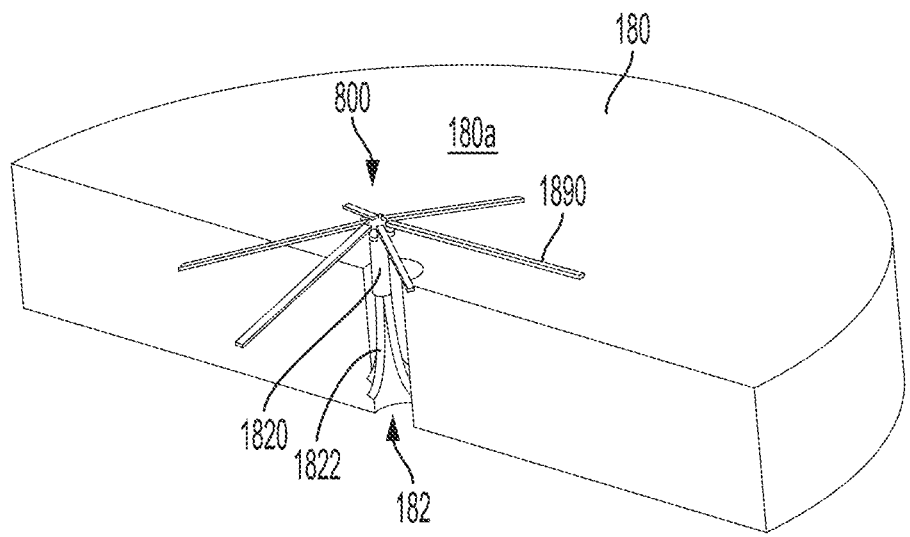

FIGS. 18A and 18B illustrate an implant deployed within a portion of anatomy, in accordance with some embodiments. In particular, a portion of anatomy 180 is illustrated generically (e.g., anatomy 180 may be the annulus of a vertebral disc or other anatomy for which there is a defect, fracture, rupture, etc., for which an implant can be used to seal). That is, the portion of anatomy can be any anatomy for which an implant may be needed to seal against leakage (e.g., a spinal vertebral disc) and is therefore illustrated schematically in FIGS. 18A and 18B. Anatomy 180 comprises an insertion corridor 182, which may be, for example, a defect in the annulus of a vertebral disc through which implant 800 is inserted, or may be a defect to other anatomy in need of leakage prevention.

Implant 800 may be similar to or the same as exemplary implant 600 discussed in connection with FIGS. 16A-C, or may include features of other implants described herein. As illustrated, after implant 800 is inserted and deployed (i.e., transitioned from a closed or insertion configuration to an open or deployed configuration), protrusions 1890 contact an inner surface 180a of the anatomy (e.g., the inner wall of a intervertebral disc annulus), providing an anchor that resists displacement of the implant. Protrusions 1890 additionally may interact with any biological material to prevent leakage of material through insertion corridor 182.

As illustrated in FIG. 18B, strands 1822 remain partially or wholly within insertion corridor 182 (but not extending below the corridor, which is external to the anatomy) and, when deployed, spread outwardly to contact the walls of the insertion corridor. In this manner, strands 1822 provide contact friction against the walls to generally resist movement of the implant to improve displacement prevention of the implant back through the insertion corridor. Additionally, strands 1822 may also interact with any material entering the insertion corridor to facilitate prevention of leakage of the material from the insertion corridor and external to anatomy 180. As shown, when deployed, body 1820 may remain partially within the insertion corridor. However, in other embodiments (e.g., in embodiments in which a portion of the body has been eliminated, such as the exemplary implant 700 illustrated in FIG. 17), the body may be inserted entirely through the insertion corridor with the strands extending downward into the insertion corridor (e.g., into the defect of a herniated vertebral disc).

Figure 19A:
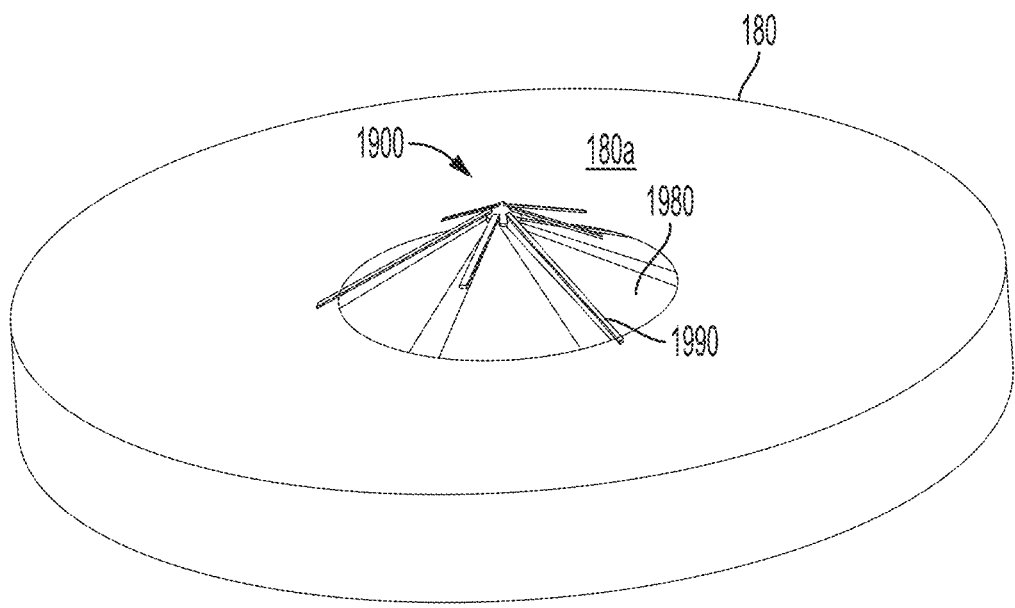
FIGS. 19A and 19B illustrate a device comprising an implant and a covering coupled thereto deployed in connection with biological anatomy, in accordance with some embodiments.
Figure 19B:
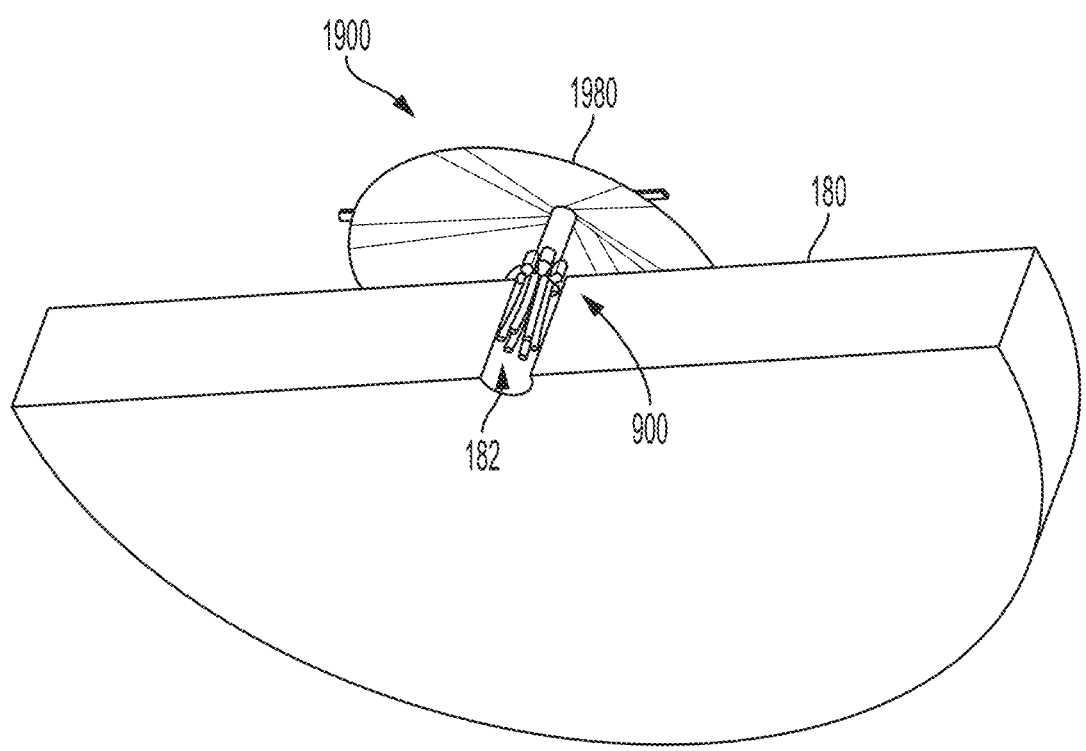

FIGS. 19A and 19B illustrate a device comprising an implant and a covering deployed in biological anatomy to seal a defect in the anatomy, in accordance with some embodiments. In particular, device 1900 comprises an implant 900 having a covering 1980 coupled thereto. Implant 900 may be similar to, or the same as, any of the exemplary implants discussed in connection with FIGS. 16A-C and 18A-B, for example. Covering 1980 may be similar to, or the same as, the covering illustrated in FIG. 15A-C, for example. As illustrated, after device 1900 is inserted and deployed (i.e., transitioned to an open or deployed configuration), covering 1980 may at least partially contact an inner surface 180a of anatomy 180. As a result, covering 1980, in conjunction with protrusions 1990, provide an anchor that resist displacement of device 1900. Covering 1980 and/or protrusions 1990 additionally may interact with surrounding biological material to assist in preventing leakage of material through insertion corridor 182 (a defect in a vertebral disc, for example). In addition, covering 1980 may physically cover the insertion corridor to prevent material from reaching the insertion corridor and leaking out of the anatomy.

According to some embodiments, device for implanting may be reinforced by filling bio-compatible material that surrounds and adheres the implant to an insertion corridor of biological anatomy through which an implant is inserted. This filler may comprise biological glues based on collagen, seaweed and/or may comprise biological glues that changes their properties under contact with materials like blood, water, or even double based materials that cure by imposing external energy or radiation, such as heat, UV radiation, etc. For example, FIGS. 20 and 21 illustrate embodiments in which a biocompatible substance (e.g., a filler) is placed or injected or cured around the body of the implant to adhere and promote recovery of the tissue in and around, for example, a defect, fracture or rupture of the annulus of biological anatomy, such as an intervertebral disc.

Figure 20:
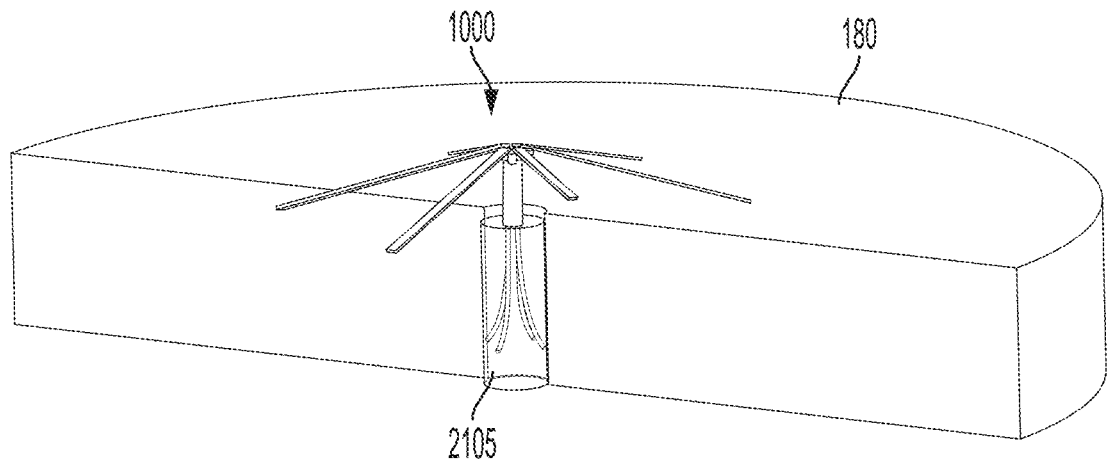
FIG. 20 illustrates an implant deployed in connection with biological anatomy to which a filler has been applied, in accordance with some embodiments.
Figure 21:
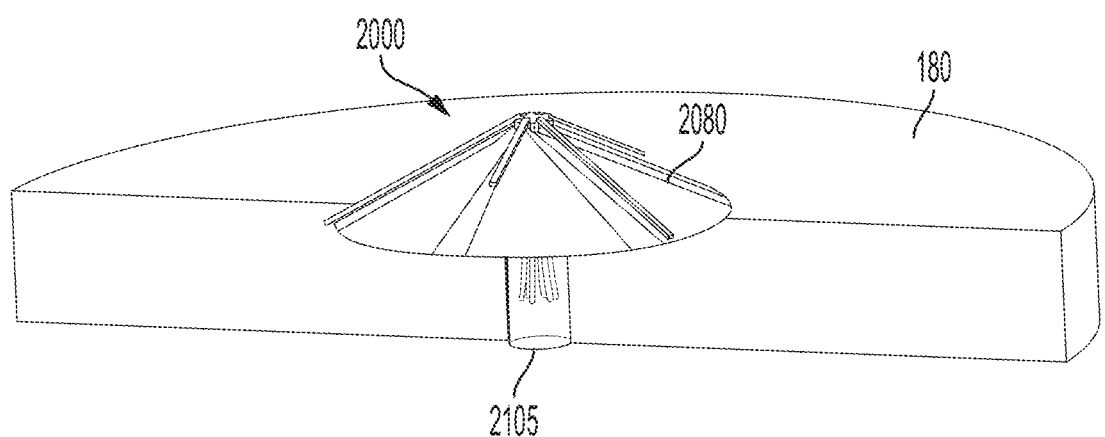
FIG. 21 illustrates a device comprising an implant and a covering coupled thereto deployed in connection with biological anatomy to which a filler has been applied, in accordance with some embodiments.

In particular, FIG. 20 illustrates an implant 1000 and FIG. 21 illustrates a device 2000 comprising the implant 1000 and a covering 2080 coupled thereto after insertion and deployment in biological anatomy 180. The implant is reinforced with a filler 2105 that works in conjunction with the implant to improve the sealing of the insertion corridor, e.g., a defect or fracture in anatomy 180, and to facilitate healing of the defect or fracture. The filler material may be applied pre-insertion, simultaneously with insertion of the implant and/or after the implant has been inserted and deployed.

It should be appreciated that while the exemplary coverings described herein are shown coupled to the exemplary implant illustrated herein, the techniques of coupling, either directly or indirectly, one or more coverings to an implant may be used with any implant having a body, protrusion and/or support apparatus to which a covering can be coupled, as the aspects are not limited for use with any particular type of implant. It should be appreciated that certain features, which are, for clarity, described in the context of separate embodiments, may also be provided in combination in a single embodiment. Conversely, various features which are, for brevity, described in the context of a single embodiment, may also be provided separately or in any suitable sub-combination.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The invention claimed is:

1. A device comprising:
   an implant configured for insertion into a portion of biological anatomy, the implant comprising:
   a body having a distal end and a proximal end; and
   a plurality of protrusions configured to extend outward from the body in a deployed configuration when inserted into the portion of the biological anatomy to resist leakage of biological material and/or to improve resistance to displacement of the implant, the plurality of protrusions comprising:
  a first plurality of protrusions coupled at the distal end of the body and extending in a direction towards the proximal end of the body; and
  a second plurality of protrusions coupled at the proximal end of the body and extending in a direction towards the distal end of the body; and
at least one covering coupled to the implant, the at least one covering comprising a first covering coupled at the distal end of the body and extending towards the proximal end of the body, the first covering having a conical and/or frustoconical shape that covers the distal end of the body and defines an inner volume that surrounds and encompasses one or more of the first plurality of protrusions when the implant is deployed in the portion of the biological anatomy.

2. The device of claim 1, wherein the inner volume defined by the first covering surrounds and encompasses a distal end of one or more of the second plurality of protrusions.

3. The device of claim 1, wherein the inner volume defined by the first covering does not encompass a proximal end of one or more of the first plurality of protrusions.

4. The device of claim 1, wherein the first covering provides an umbrella or hood over at least a portion of each of the plurality of protrusions.

5. The device of claim 1, wherein the at least one covering comprises one or more sheets of material.

6. The device of claim 1, wherein the at least one covering comprises a second covering coupled proximally from the first covering.

7. The device of claim 6, wherein the first covering provides an umbrella over at least a portion of the first plurality of protrusions and the second covering provides a skirt around a portion of the body of the implant.

8. The device of claim 6, wherein the second covering has a first opening at a distal end of the second covering to fit around a portion of the body of the implant that is proximal to one or more of the first plurality of protrusions.

9. The device of claim 1, wherein the first covering is tied to at least one of the plurality of protrusions.

10. The device of claim 1, wherein the plurality of protrusions are constructed using a first material and the at least one covering comprises a material different than the first material.

11. The device of claim 1, wherein the at least one covering comprises a one or more sheets of fabric composed of a polymer, synthetic material, a biological substance and/or is based on human tissue.

12. The device of claim 1, wherein the at least one covering comprises flexible and/or conformable fabric material.

13. The device of claim 1, wherein the at least one covering is coupled to the implant prior to insertion of the implant into the portion of the human anatomy.

14. The device of claim 1, wherein the at least one covering is coupled to the implant after insertion of the implant into the portion of the human anatomy.

15. The device of claim 1, wherein the implant is configured to be inserted into an intervertebral disc through a defect in the disc.

16. The device of claim 1, wherein the at least one covering is configurable between an insertion configuration suitable for insertion into the portion of the biological anatomy and a deployed configuration configured to facilitate prevention of leakage of biological material and/or to resist displacement of the implant.

17. The device of claim 16, wherein the insertion configuration is suitable for insertion into an intervertebral disc via a defect in the disc and the deployed configuration is configured to facilitate prevention of leakage of biological material from the intervertebral disc and/or to resist displacement of the implant from its deployed position within the intervertebral disc.

18. The device of claim 17, wherein the plurality of protrusions are configurable between an insertion configuration in which the plurality of protrusions are positioned close to the body of the implant and the deployed configuration in which the plurality of protrusions extend outward from the body to facilitate prevention of leakage of biological material from the intervertebral disc and/or to resist displacement of the implant from its deployed position within the intervertebral disc.

19. The device of claim 18, wherein the at least one covering is coupled to the plurality of protrusions such that transitioning the plurality of protrusions from the insertion configuration to the deployed configuration causes the at least one covering to transition from the insertion configuration to the deployed configuration.

20. The device of claim 19, wherein when the implant is deployed in the intervertebral disc, the at least one covering and the plurality of protrusions are positioned within the annulus of the intervertebral disc.

21. The device of claim 16, wherein the plurality of protrusions are configurable between an insertion configuration in which the plurality of protrusions are positioned close to the body of the implant and the deployed configuration in which the plurality of protrusions extend outward from the body to facilitate prevention of leakage of biological material and/or to resist displacement of the implant from its deployed position within the portion of the biological anatomy.

22. The device of claim 21, wherein the at least one covering is coupled to the plurality of protrusions such that transitioning the plurality of protrusions from the insertion configuration to the deployed configuration causes the at least one covering to transition from the insertion configuration to the deployed configuration.

* * * * *